US008685934B2

(12) United States Patent
Strumph et al.

(10) Patent No.: US 8,685,934 B2
(45) Date of Patent: Apr. 1, 2014

(54) METHODS FOR TREATING EXTREME INSULIN RESISTANCE IN PATIENTS RESISTANT TO PREVIOUS TREATMENT WITH OTHER ANTI-DIABETIC DRUGS EMPLOYING AN SGLT2 INHIBITOR AND COMPOSITIONS THEREOF

(75) Inventors: Paul Strumph, Pennington, NJ (US); Stephanie Moran, Princeton, NJ (US); James List, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/321,103

(22) PCT Filed: May 26, 2010

(86) PCT No.: PCT/US2010/036120
§ 371 (c)(1),
(2), (4) Date: Nov. 17, 2011

(87) PCT Pub. No.: WO2010/138535
PCT Pub. Date: Dec. 2, 2010

(65) Prior Publication Data
US 2012/0071403 A1 Mar. 22, 2012

Related U.S. Application Data
(60) Provisional application No. 61/181,442, filed on May 27, 2009.

(51) Int. Cl.
*A61K 31/70* (2006.01)
*A61K 38/28* (2006.01)
*A61K 31/33* (2006.01)
*A61K 31/155* (2006.01)

(52) U.S. Cl.
USPC .................. 514/23; 514/25; 514/27; 514/5.9; 514/183; 514/635

(58) Field of Classification Search
USPC ........ 514/6.47, 183, 635, 866, 5.9, 23, 25, 27
See application file for complete search history.

(56) References Cited

U.S. PATENT DOCUMENTS 6,414,126 B1 * 7/2002 Ellsworth et al. ............ 536/17.2
6,515,117 B2 * 2/2003 Ellsworth et al. ............ 536/17.2
6,936,590 B2 * 8/2005 Washburn et al. .............. 514/25

FOREIGN PATENT DOCUMENTS

WO      WO 03/099863 A1    12/2003
WO      WO 2008/116179 A1   9/2008

OTHER PUBLICATIONS

Ashworth, Doreen M. et al.: "2-Cyanopyrrolidides As Potent, Stable Inhibitors of Dipptidyl Peptidase IV," Bioorganic & Medicinal Chemistry Letters (1996), vol. 6, No. 10, pp. 1163-1166.
Ashworth, Doreen M. et al.: "4-*Cyanothiazolidides as Very Potent, Stable Inhibitors of Dipeptidyl Peptidase IV," Bioorganic & Medical Chemistry Letters (1996), vol. 6, No. 22, pp. 2745-2748.
Biller, Scott A. et al.: "Squaliene Synthase Inhibitors," Current Pharmaceutical Design (1996), vol. 2, pp. 1-40.
Biller, Scott A. et al.: "Isoprenoid (Phosphinylmethyl) phosphonates as Inhibitors of Squalene Synthetase," Journal of Medicinal Chemistry (Oct. 1988), vol. 31, No. 10, pp. 1869-1871.
Brown, G.K.: "Glucose transporters: Structure, function and consequences of deficiency," J. Inherit. Metab. Dis. (2000) vol. 23, pp. 237-246.
Buse, John, MD, PhD: "A Symposium: Combining Insulin and Oral Agents," The American Journal of Medicine (Apr. 17, 2000), vol. 108(6A), pp. 23S-32S.
Capson, Tedd Leo: "Synthesis and Evaluation of Ammonium Analogs of Carbocationic Intermediates in Squalene Biosynthesis," a dissertation submitted to the faculty of The University of Utah in partial fulfillment of the requirements for the degree of Doctor of Philosophy, Department of Medicinal Chemistry, The University of Utah, Jun. 1987.
Corey, E.J. and Volante, R.P.: "Effect of Photoselection on Fluorescence-Detected Circular Dichroism," Department of Chemistry, Harvard University, Cambridge, Massachusetts.
Ghiselli, Giancarlo et al.: "The Pharmacological Profile of FCE 27677: A Novel ACAT Inhibitor with Potent Hypolipidemic Activity Mediated by Selective Suppression of the Hepatic Secretion of ApoB-100-Containing Lipoprotein," Cardiovascular Drug Reviews, (1998), vol. 16, No. 1, pp. 16-30.
Han, Songping et al.: "Dapagliflozin, a Selective SGLT2 Inhibitor, Improves Glucose Homeostasis in Normal and Diabetic Rats," Diabetes (Jun. 2008) vol. 57, pp. 1723-1729.
Hara, Seijiro: "Ileal Na+/bile acid cotransporter inhibitors," Drugs of the Future (1999), vol. 24, No. 4, pp. 425-430.
Holman, Rury R. et al.: "Addition of Biphasic, Prandial, or Basal Insulin to Oral Therapy in Type 2 Diabetes," The New England Journal of Medicine (Oct. 25, 2007), vol. 357, No. 17, pp. 1716-1730.
Hongu, Mitsuya et al.: "Na+-Glucose Cotransporter Inhibitors as Antidibetic Agents. II1) Synthesis and Structure—Activity Relationships of 4'-Dehydroxyphlorizin Derivatives," Chemistry Pharm. Bull. (1988) vol. 46, No. 1, pp. 22-23.
Hongu, Mitsuya et al.: "Na+=Glucose Contrasporter Inhibitors as Antidibetic Agents. III.1) Synthesis and Pharmacological Properties of 4'-Derivatives Modified at the OH Groups of the Glucose Moiety," Chem. Pharm. Bull. (1998), vol. 46, No. 10, pp. 1545-1555.

(Continued)

*Primary Examiner* — Kevin E Weddington
(74) *Attorney, Agent, or Firm* — McDonnell Boehnen Hulbert & Berghoff LLP

(57) ABSTRACT

The invention provides methods for treating a patient having type 2 diabetes who has failed on previous regimens of one or more oral and/or injectable anti-diabetic agents, which include the step of administering a therapeutically effective amount of an SGLT2 inhibitor alone or in combination with another anti-diabetic agent and/or other therapeutic agent to such patient. A pharmaceutical composition containing dapagliflozin or dapagliflozin-S-propylene glycol solvate and one or more diabetic agents and/or other therapeutic agents for use in the methods of the invention is also provided.

13 Claims, No Drawings

(56) References Cited

OTHER PUBLICATIONS

Hughes, Thomas E. et al: "NVP-DPP728 (1-[[[2-[5-Cyanopyridin-2-yl)amino]ethyl]amino]acetyl]-2-cyano-(S)-pyrrolidine), a Slow-Binding Inhibitor of Dipeptidyl Peptidase IV," Biochemistry (1999), vol. 38, pp. 11597-11603.

Kanai, Yoshikatsu et al.: "The Human Kidney Low Affinity Na+/glucose Cotransporter SGLT2 Delineation of the Major Renal Reabsorptive Mechanism for D-Glucose," J. Clin. Invest. (Jan. 1994), vol. 93, pp. 397-404.

Katsuno, Kenji et al.: "Sergliflozin, a Novel Selective Inhibitor of Low-Affinity Sodium Glucose Contransporter (SGLT2), Validates the Critical Role of SGLT2 in Renal Glucose Reabsorption and Modulates Plasma Glucose Level," The Journal of Pharmacology and Experimental Therapeutics (2007) vol. 320, No. 1, pp. 323-330.

Komoroski, B. et al.: "Dapagliflozin, a Novel, Selective SGLT2 Inhibitor Improved Glycemic Control Over 2 Weeks in Patients With Type 2 Diabetes Mellitus," Clinical Pharmacology & Therapeutics (May 2009) vol. 85, No. 5, pp. 513-519.

Komoroski, B. et al.: "Dapagliflozin, a Novel, Selective SGLT2 Inhibitor Indices Dose-Dependent Glucosuria in Healthy Subjects," Clinical Pharmacology & Therapeutics (May 2009) vol. 85, No. 5, pp. 520-526.

Koro, Carol E. and Bowlin, Steven J.: "Glycemic Control From 1988-2000 Among U.S. Adults Diagnosed With Type 2 Diabetes," Diabetes Care (Jan. 2004) Diabetes Care, vol. 27, No. 1, pp. 17-20.

Krause, Brian R. and Bocan, Thomas M. A.: "ACAT INHIBITORS: Physiologic Mechanisms For Hypolipidemic and Anti-ATherosclerotic Activities in Experimental Animals," Inflammation Mediators and Pathways (1995), Chapter 6, pp. 173-198.

List, James F. et al.: "Dapagliflozia-Induced Glucosuria Is Accompanied by Weight Loss in Type 2 Diabetes Patients," Clinical Therapeutics/New Technology—Pharmacologic Treatment of Diabetes or Its Complications, p. A138, Diabetes. 57 (Suppl. 1): 138 abstr. 461-P, Jun. 2008.

Makimattila, S. et al.: "Causes of weight gain during insulin therapy with and without metformin in patients with Type II diabetes mellitus," Diabetologia (1999) vol. 42, pp. 406-412.

McClard, Ronald W. and Fujita, Thomas S.: "Novel Phosphonylphosphinyl (P-C-P-C) Analogues fo Biochemically Interesting Diphosphates. Syntheses and Properites of P-C-P-C-Analouges of Isopentenyl Diphosphate and Dimethylallyl Diphosphate," J. Am. Chem. Soc. (1987) vol. 109, pp. 5544-5545.

Meng, Wei et al.: "Discovery of Dapagliflozin: A Potent, Selective Renal Sodium-Dependent Glucose Contransporter 2 (SGLT2) Inhibitor for the Treatment of Type 2 Diabetes," J. Med. Chem. (2008) vol. 51, pp. 1145-1149.

Murakami, Koji et al.: "A Novel Insulin Sensitizer Acts as a Coligand for Peroxisome Proliferator-Activated Receptorx-x(PPAR-x) and PPAR-y—Effect of PPAR-x Activation on Abnormal Lipid Metabolism in Liver of Sucker Fatty Rats," Diabetes (Dec. 1998) vol. 47, pp. 1841-1847.

Nicolosi, Robert J. et al.: "The ACAT inhibitor, Cl-1011 is effective in the prevention and regression of aortic fatty streak area in hamsters," Atherosclerosis (1998) vol. 137, pp. 77-85.

Oku, Akira et al.: "T-1095, an Inhibitor of Renal Na+-Glucose Contrasporters, May Provide a Novel Approach to Treating Diabetes," Diabetes (Sep. 1999) vol. 48, pp. 1794-1800.

Ortiz de Montellano, Paul R. et al.: "Inhibition of Squalene Synthetase by Farnesyl Pyrophosphate Analogues," Journal of Medicinal Chemistry (1977) vol. 20, No. 2, pp. 243-249.

Poulsen, Mikael K. and Henriksen, Jan E.: "The Combined Effect of Triple Therapy With Rosiglitazone, Metformin, and Insulin Aspart in Type 2 Diabetic Patients," Diabetes Care (Dec. 2003) vol. 26, No. 12, pp. 3273-3279.

Rosenblum, Stuart B. et al.: "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A designed, Potent, Orally Active inhibitor of Cholesterol Absorption," J. Med. Chem. (1998) vol. 41, pp. 973-980.

Ryan, Michael J. et al.: "HK-2: An immortalized proximal tubule epithelial cell line from normal adult human kidney," Kidney International (1994), Vo. 45, pp. 48-57.

Salisbury, Brian G. et al.: "Hypocholesterolemic activity of a novel inhibitor of cholesterol absorption, SCH 48461," Atherosclerosis (1995) vol. 115, pp. 45-63.

Sliskovic, Drago R. and Trivedi, Bharat K.: "ACAT Inhibitors: Potential Anti-atherosclerotic Agents," Current Medicinal Chemistry (1994) vol. 1, pp. 204-225.

Smith, CI. et al.: "RP 73163: A Bioavailable Alkysulphinyl-Diphenylimidazole ACAT Inhibitor," Biorganic & Medicinal Chemistry Letters (1996) vol. 6, No. 1, pp. 47-50.

Sorbera, L.A. et al.: "Treatment of Lipoprotein Disorders ACAT Inhibitor," Drugs of the Future (1999) vol. 24, No. 1-pp. 9-15.

Stout, David M.: "Condensation of the Research," ACAT Inhibitors (Nov./Dec. 1995), pp. 359-362.

Tsujihara, Kenji et al.: "Na+=Glucose Contransporter Inhibitors as Antidiabetics. I. Synthesis and Pharmacological Properties of 4'-Dehydroxyphlorizin Derivatives Based on a New Concept," Chem. Pharm. Bull. (1996), vol. 44, No. 6, pp. 1174-1180.

Unger, Roger H.: "Reinventing Type 2 Diabetes, Pathogenesis, Treatment and Prevention," JAMA (Mar. 12, 2008) vol. 299, No. 10, pp. 1185-1187.

Yamada, Masaki et al.: "A Potent Dipeptide inhibitor of Dipeptidyl Peptidase IV," Bioorganic & Medicinal Chemistry Letters (1998) vol. 8, pp. 1537-1540.

Abdul-Ghani M.A. et al.: "Inhibition of renal glucose reabsorption: A novel strategy for achieving glucose control in type 2 diabetes mellitus," Endocrine Practice 20008 Endocrine Practice USA, vol. 14, No. 6 (Sep. 2008), pp. 782-790.

Isaji Masayuki: "Sodium-glucose cotransporter inhibitors for diabetes," Current Opinion in Investigational Drugs, Pharmapress, US, vol. 8, No. 4 (Apr. 1, 2007), pp. 285-292.

* cited by examiner

METHODS FOR TREATING EXTREME INSULIN RESISTANCE IN PATIENTS RESISTANT TO PREVIOUS TREATMENT WITH OTHER ANTI-DIABETIC DRUGS EMPLOYING AN SGLT2 INHIBITOR AND COMPOSITIONS THEREOF

This application is a U.S. National Phase Application pursuant to 35 U.S.C. §371 of International Application No. PCT/US2010/036120, filed May 26, 2010, which claims a benefit of priority from U.S. Provisional Application No. 61/181,442, filed May 27, 2009, the entire disclosure of which is herein incorporated by reference.

FIELD OF THE INVENTION

The present invention provides a method for treating type 2 diabetes in a mammal who has failed in therapy with one or more oral and/or injectable anti-diabetic agents, employing an SGLT2 inhibitor alone or in combination with another antidiabetic agent and/or other therapeutic agent, and to a pharmaceutical composition for use in such method.

BACKGROUND OF THE INVENTION

Hyperglycemia, that is, elevated plasma glucose, is a hallmark of diabetes. Plasma glucose is normally filtered in the kidney in the glomerulus but is actively reabsorbed in the proximal tubule (kidney). Sodium-dependent glucose co-transporter SGLT2 appears to be the major transporter responsible for the reuptake of glucose at this site. The SGLT inhibitor phlorizin, and closely related analogs, inhibit this reuptake process in diabetic rodents and dogs, resulting in normalization of plasma glucose levels by promoting glucose excretion without hypoglycemic side effects. Long term (6 month) treatment of Zucker diabetic rats with an SGLT2 inhibitor has been reported to improve insulin response to glycemia, improve insulin sensitivity, and delay the onset of nephropathy and neuropathy in these animals, with no detectable pathology in the kidney and no electrolyte imbalance in plasma. Selective inhibition of SGLT2 in diabetic patients would be expected to normalize plasma glucose by enhancing the excretion of glucose in the urine, thereby improving insulin sensitivity and delaying the development of diabetic complications.

The treatment of diabetes is an important health concern and despite a wide range of available therapies, the epidemic continues. Type 2 diabetes (T2DM) is a progressive disease caused by insulin resistance and decreased pancreatic β-cell function. Insulin is produced by the pancreatic β-cell and mediates cellular glucose uptake and clearance. Insulin resistance is characterized by the lack of response to the actions of this hormone which results in decreased cellular clearance of glucose from the circulation and overproduction of glucose by the liver.

The currently available therapies to treat type 2 diabetes augment the action or delivery of insulin to lower blood glucose. However, despite therapy, many patients do not achieve control of their type 2 diabetes. According to the National Health and Nutrition Examination Survey (NHANES) III, only 36% of type 2 diabetics achieve glycemic control defined as a A1C<7.0% with current therapies. In an effort to treat type 2 diabetes, aggressive therapy with multiple pharmacologic agents may be prescribed. The use of insulin plus oral agents has increased from approximately 3 to 11% from NHANES II to III.

Thus, treatment of hyperglycemia in type 2 diabetes (T2DM) remains a major challenge, particularly in patients who require insulin as the disease progresses. Various combinations of insulin with oral anti-diabetic agents (OADs) have been investigated in recent years, and an increasing number of patients have been placed on these regimens. Poulsen, M. K. et al., "The combined effect of triple therapy with rosiglitazone, metformin, and insulin in type 2 diabetic patients", *Diabetes Care*, 26 (12):3273-3279 (2003); Buse, J., "Combining insulin and oral agents", *Am. J. Med.*, 108 (Supp. 6a):23S-32S (2000). Often, these combination therapies become less effective in controlling hyperglycemia over time, particularly as weight gain and worsening insulin resistance impair insulin response pathways.

Hypoglycemia, weight gain, and subsequent increased insulin resistance are significant factors that limit optimal titration and effectiveness of insulin. (Holman, R. R. et al., "Addition of biphasic, prandial, or basal insulin to oral therapy in type 2 diabetes", *N. Engl. J. Med.*, 357 (17):1716-1730 (2007)). Weight gain with insulin therapy is predominantly a consequence of the reduction of glucosuria, and is thought to be proportional to the correction of glycemia. (Makimattila, S. et al., "Causes of weight gain during insulin therapy with and without metformin in patients with Type II diabetes mellitus", *Diabetologia*, 42 (4):406-412 (1999)). Insulin drives weight gain when used alone or with OADs. (Buse, J., supra). In some cases, intensive insulin therapy may worsen lipid overload and complicate progression of the disease through a spiral of caloric surplus, hyperinsulinemia, increased lipogenesis, increased adiposity, increased insulin resistance, beta-cell toxicity, and hyperglycemia. (Unger, R. H., "Reinventing type 2 diabetes: pathogenesis, treatment, and prevention", *JAMA*, 299 (10):1185-1187 (2008)). Among commonly used OADs, thiazolidinediones (TZDs) and sulfonylureas intrinsically contribute to weight gain as glucosuria dissipates with improved glycemic control. Weight gain is less prominent with metformin, acting through suppression of hepatic glucose output, or with incretin-based DPP-4 inhibitors. Overall, there is a pressing need for novel agents that can be safely added to insulin-dependent therapies to help achieve glycemic targets without increasing the risks of weight gain or hypoglycemia.

A novel approach to treating hyperglycemia involves targeting transporters for glucose reabsorption in the kidney. (Kanai, Y. et al., "The human kidney low affinity Na+/glucose cotransporter SGLT2. Delineation of the major renal reabsorptive mechanism for D-glucose", *J. Clin. Invest.*, 93 (1): 397-404 (1994)). Agents that selectively block the sodium-glucose cotransporter 2 (SGLT2) located in the proximal tubule of the kidney can inhibit reabsorption of glucose and induce its elimination through urinary excretion. (Brown, G. K., "Glucose transporters: structure, function and consequences of deficiency", *J. Inherit. Metab. Dis.*, 23 (3):237-246 (2000)). SGLT2 inhibition has been shown in pre-clinical models to lower blood glucose independently of insulin. (Han, S. et al., "Dapagliflozin, a selective SGLT2 inhibitor, improves glucose homeostasis in normal and diabetic rats", *Diabetes*, 57 (6):1723-1729 (2008); Katsuno, K. et al., "Sergliflozin, a novel selective inhibitor of low-affinity sodium glucose cotransporter (SGLT2), validates the critical role of SGLT2 in renal glucose reabsorption and modulates plasma glucose level", *J. Pharmacol. Exp. Ther.*, 320 (1):323-330 (2007)).

Dapagliflozin (which is disclosed in U.S. Pat. No. 6,515, 117) is an inhibitor of sodium-glucose reabsorption by the kidney, by inhibiting SGLT2, which results in an increased excretion of glucose in the urine. This effect lowers plasma glucose in an insulin-independent manner.

Dapagliflozin is currently undergoing clinical development for treatment of type 2 diabetes. (Han, S. et al., supra; Meng, W. et al., "Discovery of dapagliflozin: a potent, selective renal sodium-dependent glucose cotransporter 2 (SGLT2) inhibitor for the treatment of type 2 diabetes", *J. Med. Chem.*, 51 (5):1145-1149 (2008)). Phase 2a and 2b studies with dapagliflozin have demonstrated efficacy in reducing hyperglycemia either alone or in combination with metformin in patients with T2DM. (Komoroski, B. et al., "Dapagliflozin, a novel, selective SGLT2 inhibitor, improved glycemic control over 2 weeks in patients with type 2 diabetes mellitus", *Clin. Pharmacol. Ther.*, 85 (5):513-519 (2009); List, J. F. et al., "Dapagliflozin-induced glucosuria is accompanied by weight loss in type 2 diabetic patients", 68th Scientific Sessions of the American Diabetes Association, San Francisco, Calif., Jun. 6-10, 2008, Presentation No. 0461P).

It has been found that dapagliflozin does not act through insulin signaling pathways and is effective in controlling blood sugar in patients whose insulin signaling pathways do not work well. This applies to extremes of insulin resistance, in type 2 diabetes as well as in insulin resistance syndromes, caused by, for example, mutations in the insulin receptor.

BRIEF DESCRIPTION OF THE INVENTION

In accordance with the present invention, a method is provided for treating type 2 diabetes in a mammalian subject or patient, including a human subject or patient, who has failed in previous treatment with one or more oral anti-diabetic agents and/or an injectable anti-diabetic agents (which may include insulin), which includes the step of administering to a mammalian subject or patient in need of such treatment a therapeutically effective amount of an SGLT2 inhibitor.

In certain embodiments, the inventive methods for treating type 2 diabetes in a mammalian subject or patient, including a human subject or patient, who has failed in previous treatment with one or more anti-diabetic agents, includes the step of administering a therapeutically effective amount of dapagliflozin or dapagliflozin propylene glycol hydrate (also referred to as dapagliflozin propylene glycol solvate or dapagliflozin-PGS).

Still further in accordance with the invention, in any of the described methods, the method includes the step of administering to a mammalian subject or patient a pharmaceutical composition which includes a therapeutically effective amount of an SGLT2 inhibitor such as dapagliflozin or dapagliflozin-PGS and at least one pharmaceutically acceptable carrier, diluent, or adjuvant. For example, in any of the methods of the invention, the method includes the step of administering to a mammalian subject or patient a pharmaceutical composition containing a therapeutically effective amount of dapagliflozin or dapagliflozin-PGS, such as from about 1 to about 200 mg/day, and at least one pharmaceutically acceptable carrier, diluent, or adjuvant.

In any of the inventive methods, the SGLT2 inhibitor such as dapagliflozin or dapagliflozin-PGS, such as from 0.5 to about 350 mg/day, can be administered in combination with one or more other oral and/or injectable anti-diabetic agents, which can be another SGLT2 inhibitor as described herein and/or can be one or more anti-diabetic agents other than an SGLT2 inhibitor, which may include insulin, and/or another or additional therapeutic agent which can be an anti-obesity agent, an anti-hyperlipidemic agent, an agent for treating atherosclerosis, an anti-hypertensive agent, and/or an anti-thrombotic or anticoagulant such as a platelet aggregation inhibitor. In one embodiment, the anti-diabetic agent(s) and/or other therapeutic agent(s) are administered in a therapeutically effective amount.

In one embodiment of the inventive methods employing a combination of an SGLT2 inhibitor(s) such as dapagliflozin or dapagliflozin-PGS and anti-diabetic agent(s), and/or another additional therapeutic agent which can be an anti-obesity agent, an anti-hyperlipidemic agent, an agent for treating atherosclerosis, an anti-hypertensive agent, and/or an antithrombotic or anticoagulant such as a platelet aggregation inhibitor, the dosage for the other anti-diabetic agent(s) (used in combination with the SGLT2 inhibitor) is from about 20% of the lowest dose normally recommended for treating diabetes up to about 100% of the normally recommended dosage for treating diabetes.

In another embodiment in the methods of the present invention, the patient is treated with an SGLT2 inhibitor such as dapagliflozin or dapagliflozin-PGS and one or more anti-diabetic agents wherein the anti-diabetic agent is selected from a biguanide, such as metformin, a sulfonyl urea, such as glyburide or glipizide, a glucosidase inhibitor, a PPAR γ agonist, a PPAR α/γ dual agonist, an aP2 inhibitor, a DPP4 inhibitor, an insulin sensitizer, such as rosiglitazone or pioglitazone, a glucagon-like peptide-1 (GLP-1) receptor agonist, glucokinase activator, a DGAT inhibitor, a CCR2 antagonist, 11-β-HSD (hydroxysteroid dehydrogenase), insulin, a meglitinide, a PTP1B inhibitor, a glycogen phosphorylase inhibitor, a glucos-6-phosphatase inhibitor, or a combination thereof.

In another embodiment, the invention provides a method of treating type 2 diabetes in a mammal, particularly a human, which includes the step of administering to the mammal an SGLT2 inhibitor such as dapagliflozin or dapagliflozin-PGS in combination with one or more anti-diabetic agents wherein the anti-diabetic agent is selected from metformin, glyburide, glimepiride, glipyride, glipizide, exenatide, chlorpropamide, gliclazide, saxagliptin, sitagliptin, vildagliptin, acarbose, miglitol, pioglitazone, rosiglitazone, insulin, G1-262570, isaglitazone, JTT-501, N,N-2344, L895645, YM-440, R-119702, AJ9677, repaglinide, nateglinide, KAD1129, AR-HO39242, GW-409544, KRP297, AC2993, LY315902 or NVP-DPP-728A, or a combination of two or more thereof.

In another embodiment of the method of the present invention, dapagliflozin or dapagliflozin-PGS at a dose within the range from about 0.5 to about 200 mg/day is administered in combination with insulin at a dose as prescribed by a physician or as disclosed in the latest *Physicians' Desk Reference* (PDR) and/or metformin at a dose within the range from about 500 to about 2000 mg/day and/or rosiglitazone (AVANDIA®, Glaxo-Wellcome) at a dose within the range from about 0.5 to about 25 mg/day or pioglitazone (ACTOS®, Takeda Pharmaceuticals America, Inc.) at a dose within the range from about 0.5 to about 75 mg/day.

In another embodiment of the method of the present invention (a) dapagliflozin or dapagliflozin-PGS at a dose from about 0.5 to about 200 mg/day is administered in combination with insulin at a dose as prescribed by a physician or as described in the PDR; or (b) dapagliflozin or dapagliflozin-PGS at a dose from about 0.5 to about 200 mg/day is administered in combination with insulin at a dose as prescribed by a physician or as described in the PDR, and metformin at a dose from about 500 to about 2000 mg/day; or (c) dapagliflozin or dapagliflozin-PGS at a dose from about 0.5 to about 200 mg/day is administered in a combination with insulin at a dose as prescribed by a physician or as described in the PDR, and pioglitazone (ACTOS®, Takeda Pharmaceuticals America, Inc.) at a dose from about 0.5 to about 75 mg/day, or rosiglitazone (AVANDIA®, Glaxo-Wellcome) at a dose from about 0.5 to about 25 mg/day; or (d) dapagliflozin or dapagliflozin-PGS at a dose from about 0.5 to about 200 mg/day is administered in combination with insulin at a dose as prescribed by a physician or as described in the PDR, metformin at a dose from about 500 to about 2000 mg/day, and pioglitazone at a dose from about 0.5 to about 75 mg/day or rosiglitazone at a dose from about 0.5 to about 25 mg/day.

Another embodiment of the invention is the use of an SGLT2 inhibitor such as dapagliflozin or dapagliflozin-PGS in the manufacture of a medicament for treating type 2 diabetes in mammals, particularly humans.

Another embodiment of the invention is the use of a combination of an SGLT2 inhibitor such as dapagliflozin or dapagliflozin-PGS and one or more anti-diabetic agents and/or one or more anti-obesity agents in the manufacture of a medicament for treating type 2 diabetes. The anti-diabetic agent and/or anti-obesity agent is administered prior to, after, or concurrently with the SGLT2 inhibitor.

Another embodiment of the invention is the use of an SGLT2 inhibitor such as dapagliflozin or dapagliflozin-PGS, in the manufacture of a medicament for the treatment of type 2 diabetes, as defined herein, in which such treatment includes the step of administering to a mammal a combination of an SGLT2 inhibitor with an anti-diabetic agent and/or anti-obesity agent, for concurrent or sequential use, in any order.

Another embodiment of the invention is the use of a combination of an SGLT2 inhibitor such as dapagliflozin or dapagliflozin-PGS and one or more anti-diabetic agents in the manufacture of a medicament for treating type 2 diabetes, as defined herein, wherein the anti-diabetic agent is a biguanide, a sulfonyl urea, a glucosidase inhibitor, a PPAR γ agonist, a PPAR α/γ dual agonist, an aP2 inhibitor, a DPP4 inhibitor, an insulin sensitizer, a glucagon-like peptide-1 (GLP-1) receptor agonist, a glucokinase activator, a DGAT inhibitor, a CCR2 antagonist, 11-β-HSD, insulin, a meglitinide, a PTP1B inhibitor, a glycogen phosphorylase inhibitor, a glucos-6-phosphatase inhibitor, or a combination of two or more thereof. The anti-diabetic agent is administered prior to, after, or concurrently with the SGLT2 inhibitor.

Another embodiment of the invention is the use of an SGLT2 inhibitor such as dapagliflozin or dapagliflozin-PGS, in the manufacture of a medicament for the treatment of type 2 diabetes, as defined herein, in which such treatment includes the step of administering to a mammalian species a combination with one or more anti-diabetic agents, for concurrent or sequential use, in any order, wherein the anti-diabetic agent is selected from a biguanide, a sulfonyl urea, a glucosidase inhibitor, a PPAR γ agonist, a PPAR α/γ dual agonist, an aP2 inhibitor, a DPP4 inhibitor, an insulin sensitizer, a glucagon-like peptide-1 (GLP-1) receptor agonist, a glucokinase activator, a DGAT inhibitor, a CCR2 antagonist, 11-β-HSD, insulin, a meglitinide, a PTP1B inhibitor, a glycogen phosphorylase inhibitor, a glucos-6-phosphatase inhibitor, or a combination of two or more thereof.

Another embodiment of the invention is the use of an SGLT2 inhibitor such as dapagliflozin or dapagliflozin-PGS in combination with another or additional therapeutic agent which is an anti-obesity agent, an anti-hyperlipidemic agent, or agent used to treat arteriosclerosis, which is an HMG CoA reductase inhibitor, a squalene synthetase inhibitor, a fibric acid derivative, aspirin, a bile acid sequestrant, an ACAT inhibitor, an upregulator of LDL receptor activity, a cholesterol absorption inhibitor, a cholesteryl transfer protein (CETP) inhibitor, an ileal Na+/bile acid cotransporter inhibitor, a phytoestrogen, a beta-lactam cholesterol absorption inhibitor, an HDL upregulator, a PPAR α-agonist and/or an FXR agonist; an LDL catabolism promoter such, a sodium-proton exchange inhibitor, an LDL-receptor inducer or a steroidal glycoside, an anti-oxidant, or an antihomocysteine agent, isoniazid, an HMG-CoA synthase inhibitor, or a lanosterol demethylase inhibitor, a PPAR δ agonist, or a sterol regulating element binding protein-I (SREBP-1); or the other therapeutic agent is an anti-hypertensive agent, which is a beta adrenergic blocker, a calcium channel blocker (L-type and/or T-type), a diuretic, a renin inhibitor, an ACE inhibitor, an AT-1 receptor antagonist, an ET receptor antagonist, a dual ET/AII antagonist, a neutral endopeptidase (NEP) inhibitor, a vasopeptidase inhibitor (dual NEP-ACE inhibitor) or a nitrate; or the other therapeutic agent is a platelet aggregation inhibitor which is clopidogrel or ticlopidine or prasugrel or aspirin.

The additional therapeutic agent is administered prior to, after or concurrently with the SGLT2 inhibitor.

Another embodiment of the invention is the use of an SGLT2 inhibitor such as dapagliflozin or dapagliflozin-PGS and another or additional therapeutic agent as defined above in the manufacture of a medicament for the treatment of type 2 diabetes.

The other or additional therapeutic agent is administered prior to, after or concurrently with the SGLT2 inhibitor.

In one embodiment of the inventive methods employing a combination of an SGLT2 inhibitor and other or additional therapeutic agent(s), the SGLT2 inhibitor is administered in a weight ratio to the other or additional therapeutic agent(s) in an amount within the range from about 200:1 to about 0.1:1. In another embodiment, the SGLT2 inhibitor is administered in a weight ratio to the other or additional therapeutic agent(s)s in an amount within the range from about 100:1 to about 0.2:1.

Another embodiment of the invention is the use of a combination of an SGLT2 inhibitor such as dapagliflozin or dapagliflozin-PGS and one or more anti-diabetic agents in the manufacture of a medicament for treating type 2 diabetes, wherein the anti-diabetic agent is selected from metformin, glyburide, glimepiride, glipyride, glipizide, chlorpropamide, gliclazide, saxagliptin, sitagliptin, vildagliptin, acarbose, miglitol, pioglitazone, rosiglitazone, insulin, Gl-262570, isaglitazone, JTT-501, exenatides, N,N-2344, L895645, YM-440, R-119702, AJ9677, repaglinide, nateglinide, KAD1129, AR-HO39242, GW-409544, KRP297, AC2993, LY315902 or NVP-DPP-728A, or a combination of two or more thereof. The anti-diabetic agent is administered prior to, after, or concurrently with the SGLT2 inhibitor.

Another embodiment of the invention is the use in the methods of the invention of a combination of an SGLT2 inhibitor such as dapagliflozin or dapagliflozin-PGS with insulin alone, metformin alone, a thiazolidinedione alone such as pioglitazone or rosiglitazone, or a combination of dapagliflozin or dapagliflozin-PGS and metformin and insulin, or a combination of dapagliflozin or dapagliflozin-PGS and insulin and a thiazolidinedione, or a combination of dapagliflozin or dapagliflozin-PGS and metformin and a thiazolidinedione, or a combination of dapagliflozin or dapagliflozin-PGS and insulin, metformin and a thiazolidinedione, where the thiazolidinedione is preferably pioglitazone or rosiglitazone.

The SGLT2 inhibitor employed in the methods of the invention may be a C-aryl glucoside (also referred to as a C-glucoside) or an O-arylglucoside (also referred to as an O-glucoside) as will be described in detail hereinafter.

In one embodiment of the inventive methods employing a combination of an SGLT2 inhibitor such as dapagliflozin or dapagliflozin-PGS and one or more anti-diabetic agent(s), the SGLT2 inhibitor is administered in a weight ratio to the other anti-diabetic agent(s) in an amount within the range of from about 200:1 to about 0.1:1. In another embodiment, the SGLT2 inhibitor is administered in a weight ratio to the other anti-diabetic agent(s) in an amount within the range of from about 100:1 to about 0.2:1.

The invention provides the use of an SLGT2 inhibitor in the manufacture of a medicament for the treatment of type 2 diabetes. In one embodiment, the invention provides the use of a C-arylglucoside or O-arylglucoside in the manufacture of a medicament and one or more anti-diabetic agents for the treatment of type 2 diabetes. For example, the invention provides the use of dapagliflozin or dapagliflozin-PGS in the manufacture of a medicament for the treatment of type 2 diabetes. In any of the described uses, the SLGT2 inhibitor is administered in a therapeutically effective amount.

The invention provides the combination of an SLGT2 inhibitor and one or more anti-diabetic agent(s) as a medicament for treating type 2 diabetes. In one embodiment, the invention provides the combination of a C-arylglucoside or O-arylglucoside and one or more anti-diabetic agent(s) as a medicament for treating type 2 diabetes. For example, the invention provides the combination of dapagliflozin or dapagliflozin-PGS and one or more anti-diabetic agent(s) as a medicament for treating type 2 diabetes. In any of the described uses, the SLGT2 inhibitor is administered in a therapeutically effective amount.

The term "extreme insulin resistance" also referred to as "severe insulin resistance", as employed herein, refers to inadequate glycemic control despite treatment with >=50 units per day insulin plus an oral insulin sensitizer (a thiazolidinedione such as pioglitazone or rosiglitazone and/or metformin).

The term "therapeutically effective amount of an SLGT2 inhibitor" as used herein refers to an amount or dose of SLGT2 inhibitor that lowers plasma glucose levels to medically acceptable levels (as determined by ADA standards) in a mammalian subject or patient.

The term "dapagliflozin-PGS" as used herein refers to dapagliflozin propylene glycol solvate or dapagliflozin propylene glycol hydrate, including the (S) form and the (R) form of dapagliflozin propylene glycol.

The term "hypoglycemia" as employed herein refers to a blood glucose level of below 60 mg per deciliter (dL).

The term "diabetes" as employed herein refers to type 2 (or Type II) diabetes or non-insulin dependent diabetes mellitus (NIDDM) wherein a patient has inadequate glycemic control ($HbA_{1c}$<7%) with diet and exercise and includes hyperglycemia and may include extreme insulin resistance.

The term "hyperglycemia" as employed herein refers to a blood glucose level of above 180 mg per deciliter (dL).

The term "failed" on previous treatment with one or more oral anti-diabetic agents and/or injectable anti-diabetic agents, refers to patients with type 2 diabetes on such previous treatment who were not able to achieve glycemic control defined as $HbA_{1c}$<7.0%.

The term "pharmaceutically acceptable carrier" as used herein means a non-toxic, inert solid, semi-solid or liquid filler, diluent, encapsulating material or formulation auxiliary of any type. Some examples of materials which can serve as pharmaceutically acceptable carriers are sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such a propylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions, as well as other non-toxic compatible lubricants, such as sodium lauryl sulfate and magnesium stearate; coloring agents; releasing agents; coating agents; sweetening; flavoring; and perfuming agents; preservatives; and antioxidants.

The invention provides pharmaceutical compositions containing an SGLT2 inhibitor preferably dapagliflozin or dapagliflozin-PGS alone or together with one or more anti-diabetic agents such as metformin and a thiazolidinedione, and/or one or more therapeutic agents, such as an anti-obesity agent, as described hereinbefore, formulated together with one or more non-toxic pharmaceutically acceptable carriers, diluents, or adjuvants for use in the methods of the invention. The pharmaceutical compositions can be formulated for oral administration in solid or liquid form, for parenteral injection or for rectal administration. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters, such as ethyl oleate. Proper fluidity can be maintained, for example, by the use of a coating such as lecithin, by the maintenance of the required particle size in the case of dispersions, and by the use of surfactants.

These compositions can also contain adjuvants, such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It can also be desirable to include isotonic agents, for example, sugars, sodium chloride and the like. Prolonged absorption of the injectable pharmaceutical form can be brought about by the use of agents delaying absorption, for example, aluminum monostearate and gelatin.

In carrying out the methods of the invention for treating mammalian subjects or patients, the SGLT2 inhibitor alone or in combination with one or more other anti-diabetic agents and/or one or more other therapeutic agents can be administered to a mammalian subject or patient in need of treatment in an amount which can be as high as an amount used to treat diabetes (elevated blood glucose levels) but less than an amount which causes hypoglycemia. The daily dose is adjusted depending upon the mammalian subject or patient and the specific SGLT2 inhibitor employed and other anti-diabetic agents employed. The dose can be lowered as successful treatment of type 2 diabetes and possibly extreme insulin resistance are achieved. In one embodiment, the SGLT2 inhibitor is administered to a mammalian subject or patient in an amount to successfully treat diabetes (elevated blood glucose levels) and less than an amount which causes hypoglycemia. For example, in one embodiment, the SGLT2 inhibitor is orally administered in an amount of from about 1 mg to about 1000 mg per day. In another embodiment, the SGLT2 inhibitor is orally administered in an amount of from about 0.5 mg to about 350 mg/day. In other embodiments, the SGLT2 inhibitor is orally administered in an amount of from about 1 to about 200 mg/day or about 2.5 mg to about 75 mg/day. In another embodiment, the SGLT2 inhibitor is orally administered in an amount of from about 5 mg to about 50 mg/day. All of the described dosages can be administered in a single dose or in the form of individual doses from 1 to 4 times per day, for example.

In one embodiment, the methods of the invention include the step of administrating the SGLT2 inhibitor dapagliflozin propylene glycol hydrate (referred to as dapagliflozin-PGS or dapa-PGS), as disclosed in U.S. application Ser. No. 11/765, 481, published as US 2008/0004336 A1, which is herein incorporated by reference in its entirety for any purpose. The dapa-PGS can be in the (S) form or the (R) form. The (S) form of dapa-PGS is shown below as Compound I:

Compound I

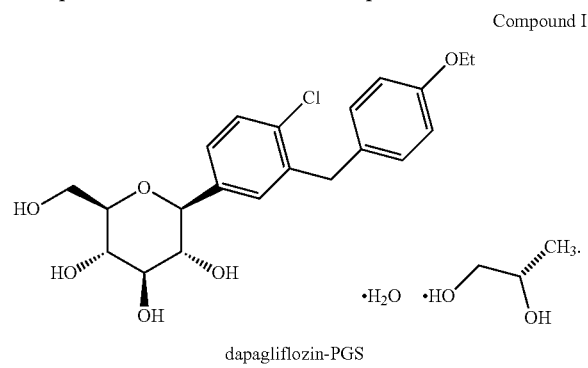

dapagliflozin-PGS

The (R) form of dapa-PGS is shown below as Compound IA:

Compound IA

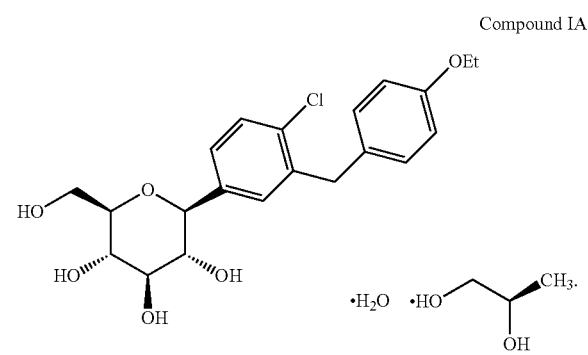

The crystalline structure of dapa-PGS is characterized by one or more of the following:

a) unit cell parameters substantially equal to the following: Cell Dimensions:
  a=11.2688(8) Å
  b=4.8093(3) Å
  c=46.723(3) Å
  α=90 degrees
  β=90 degrees
  γ=90 degrees
  Space group=$P2_12_12_1$
  Molecules/asymmetric unit=1
wherein measurement of said crystalline structure is at room temperature and which is characterized by fractional atomic coordinates substantially as listed in Table 4 of U.S. provisional application Ser. No. 60/817,118 and in U.S. non-provisional application Ser. No. 11/765,481 (US 2008/0004336 A1);

b) a powder x-ray diffraction pattern comprising 2θ values (CuKα λ=1.5418 Å) selected from the group consisting of 3.8±0.1, 7.6±0.1, 8.1±0.1, 8.7±0.1, 15.2±0.1, 15.7.4±0.1, 17.1±0.1, 18.9±0.1 and 20.1±0.1, at room temperature;

c) a solid state $^{13}C$ NMR spectrum having substantially similar peak positions at 16.2, 17.6, 39.3, 60.9, 63.3, 69.8, 76.9, 78.7, 79.4, 113.8, 123.6, 129.3, 130.5, 132.0, 135.7, 139.1 and 158.0 ppm, as determined on a 400 MHz spectrometer relative to TMS at zero;

d) a differential scanning calorimetry thermogram having an endotherm in the range of about 50° C. to 78° C. or as shown in FIG. 7 of U.S. provisional application Ser. No. 60/817,118 and in U.S. non-provisional application Ser. No. 11/765,481 (US 2008/0004336 A1);

e) thermal gravimetric analysis curve with about 18.7% weight loss from about room temperature up to about 240° C. or as shown in FIG. 5 of U.S. provisional application Ser. No. 60/817,118 and in U.S. non-provisional application Ser. No. 11/765,481 (US 2008/0004336 A1); or f) having a proton NMR having substantially similar peak positions as listed in Table 1A of U.S. provisional application Ser. No. 60/817,118 and in U.S. non-provisional application Ser. No. 11/765,481 (US 2008/0004336 A1).

SGLT2 inhibitors suitable for use in accordance with the present invention also include C-arylglucosides and O-arylglucosides.

Examples of C-arylglucoside (also referred to as C-glucosides) SGLT2 inhibitors useful in the methods of the invention, include, but are not limited to, the following:

1) C-arylglucosides as described in U.S. Pat. No. 6,515, 117 and PCT/US03/15591, the disclosures of which are incorporated herein by reference in their entireties for any purpose. In one embodiment, the C-arylglucoside is dapagliflozin or (2S,3R,4R,5S,6R)-2-(4-chloro-3-(4-ethoxybenzyl) phenyl)-6-(hydroxymethyl)tetrahydro-2H-pyran-3,4,5-triol, shown below as Compound II:

Compound II

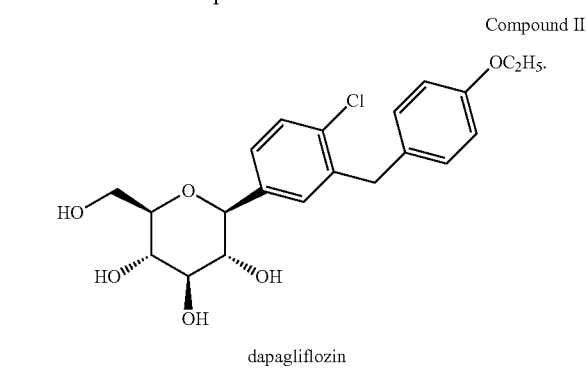

dapagliflozin

In another embodiment, the C-arylglucoside is the tetraacetate analog of dapagliflozin or (2R,3R,4R,5S,6S)-2-(acetoxymethyl)-6-(4-chloro-3-(4-ethoxybenzyl)phenyl)tetrahydro-2H-pyran-3,4,5-triyl triacetate, also disclosed in U.S. Pat. No. 6,515,117 and PCT/US03/15591, and shown below as Compound IIA:

Compound IIA

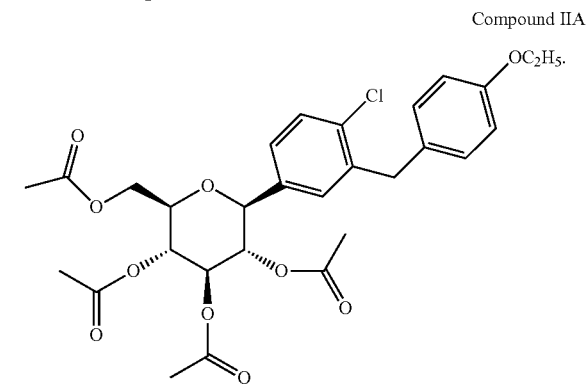

2) The C-arylglucosides, or pharmaceutically acceptable salts thereof, as described in U.S. Pat. No. 6,414,126 and PCT/US00/27187, the disclosures of which are incorporated herein by reference in their entireties for any purpose, including compounds of Formula III:

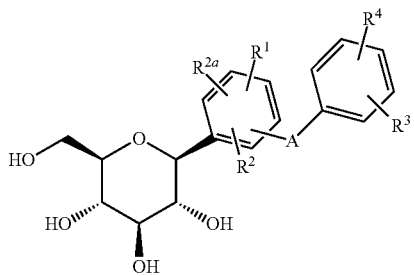

Formula III wherein $R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated 5-, 6- or 7-membered carbocycle or heterocycle which can contain 1 to 4 heteroatoms in the ring which are N, O, S, SO, and/or $SO_2$;

$R^3$ and $R^4$ are independently hydrogen, OH, $OR^{5a}$, OAryl, $OCH_2$Aryl, alkyl, cycloalkyl, $CF_3$, —$OCHF_2$, —$OCF_3$, halogen, —CN, —$CO_2R^{5b}$, —$CO_2H$, —$COR^{6b}$, —$CH(OH)R^{6c}$, —$CH(OR^{5h})R^{6d}$, —$CONR^6R^{6a}$, —$NHCOR^{5c}$, —$NHSO_2R^{5d}$, —$NHSO_2$Aryl, Aryl, —$SR^{5e}$, —$SOR^{5f}$, —$SO_2R^{5g}$, —$SO_2$Aryl, or a 5-, 6- or 7-membered heterocycle which can contain 1 to 4 heteroatoms in the ring which are N, O, S, SO, and/or $SO_2$, or $R^3$ and $R^4$ together with the carbons to which they are attached form an annelated 5-, 6- or 7-membered carbocycle or heterocycle which can contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated 5-, 6- or 7-membered heterocycle which can contain 1 to 4 heteroatoms in the ring which are N, O, S, SO, and/or $SO_2$; and A is O, S, NH, or $(CH_2)_n$ where n is 0-3, and a pharmaceutically acceptable salt thereof, all stereoisomers thereof, and all prodrug esters thereof, provided that when A is $(CH_2)_n$ where n is 0, 1, 2, or 3 or A is O, and at least one of $R^1$, $R^2$, and $R^{2a}$ is OH or $OR^5$, then at least one of $R^1$, $R^2$, and $R^{2a}$ is $CF_3$, $OCF_3$, or $OCHF_2$ and/or at least one of $R^3$ and $R^4$ is $CF_3$, —$OCHF_2$, —$OCF_3$, $CH(OR^{5h})R^{6d}$, $CH(OH)R^{6c}$, $COR^{6b}$, —CN, —$CO_2R^{5b}$, —$NHCOR^{5c}$, —$NHSO_2R^{5d}$, —$NHSO_2$Aryl, Aryl, —$SR^{5e}$, —$SOR^{5f}$, —$SO_2R^{5g}$ or —$SO_2$Aryl.

In another embodiment, the compound is (2S,3R,4R,5S,6R)-2-(4-chloro-3-(4-ethylbenzyl)phenyl)-6-(hydroxymethyl)tetrahydro-2H-pyran-3,4,5-triol disclosed in U.S. patent application Ser. No. 11/233,617 and US 2006/0063722 A1 and shown below as Compound IIIA:

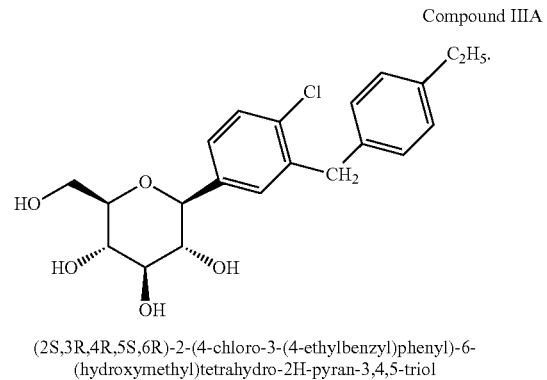 [SMILES: CCc1ccc(Cc2cc([C@@H]3O[C@H](CO)[C@@H](O)[C@H](O)[C@H]3O)ccc2Cl)cc1]

Compound IIIA (2S,3R,4R,5S,6R)-2-(4-chloro-3-(4-ethylbenzyl)phenyl)-6-(hydroxymethyl)tetrahydro-2H-pyran-3,4,5-triol 3) C-aryl glucosides that are crystalline complexes of a D- or L-amino acid as described in PCT/US02/11066, US 2003/0064935, and U.S. Pat. No. 6,774,112, the disclosures of which are incorporated herein by reference for any purpose in their entireties. The C-aryl glucosides comprise crystalline D- or L-amino acid complexes of Formula IV:

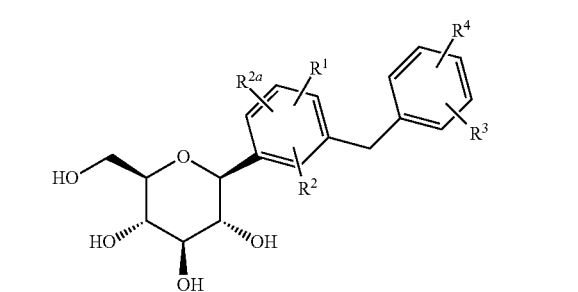

Formula IV wherein $R^1$, $R^2$ and $R^{2a}$ are independently hydrogen, OH, $OR^5$, alkyl, —$OCHF_2$, —$OCF_3$, —$SR^{5a}$ or halogen;

$R^3$ and $R^4$ are independently hydrogen, OH, $OR^{5b}$, alkyl, cycloalkyl, $CF_3$, —$OCHF_2$, —$OCF_3$, halogen, —$CONR^6R^{6a}$, —$CO_2R^{5c}$, —$CO_2H$, —$COR^{6b}$, —CH(OH) $R^{6c}$, —$CH(OR^{5d})R^{6d}$, —CN, —$NHCOR^{5c}$, —$NHSO_2R^{5f}$, —$NHSO_2$Aryl, —$SR^{5g}$, —$SOR^{5h}$, —$SO_2R^{5f}$, or a 5-, 6- or 7-membered heterocycle which can contain 1 to 4 heteroatoms in the ring which are N, O, S, SO, and/or $SO_2$, or $R^3$ and $R^4$ together with the carbons to which they are attached form an annelated 5-, 6- or 7-membered carbocycle or heterocycle which can contain 1 to 4 heteroatoms in the ring which are N, O, S, SO, $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated 5-, 6- or 7-membered heterocycle which can contain 1 to 4 heteroatoms in the ring which are N, O, S, SO, and/or $SO_2$, which are disclosed as being useful for treating obesity.

In one embodiment, the crystalline amino acid complexes include the L-proline, L-phenylalanine, and D-phenylalanine complexes where $R^{2a}$, $R^2$, and $R^4$ are hydrogen, $R^1$ is 4-Cl, and $R^3$ is 4-$C_2H_5$ or 4-$OC_2H_5$.

4) The glucopyranosyl-substituted benzene derivatives of Formula V or pharmaceutically acceptable salts thereof, as described in US 2005/0209166, the disclosure of which is incorporated by reference in its entirety for any purpose, Formula V

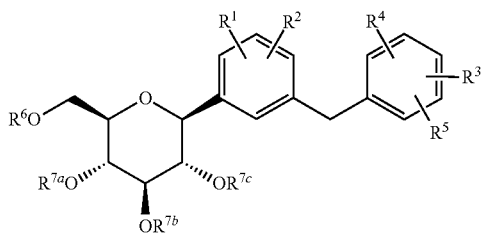

wherein $R^1$, $R^2$, $R^3$, $R^4$, $R^5$, $R^6$, $R^{7a}$, $R^{7b}$ and $R^{7c}$ are as defined in US 2005/0209166.

5) D-pyranosyl-substituted phenyl compounds of Formula VI or pharmaceutically acceptable salts thereof, as described in US 2006/0074031, the disclosure of which is incorporated herein by reference in its entirety for any purpose, Formula VI

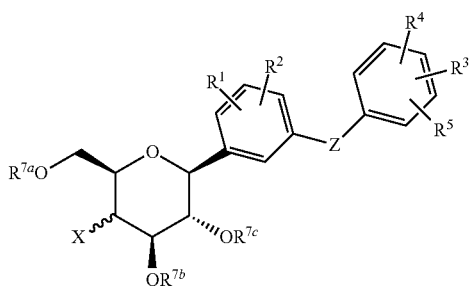

wherein $R^1$, $R^2$, $R^3$, $R^4$, $R^5$, $R^{7a}$, $R^{7b}$, $R^{7c}$, X and Z are as defined in US 2006/0074031.

6) D-xylopyranosyl-substituted compounds of Formula VII or pharmaceutically acceptable salts thereof, as described in US 2006/0035841, the disclosure of which is incorporated herein by reference for any purpose, Formula VII

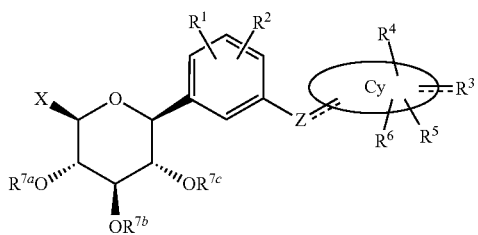

wherein $\doteq$ denotes a single or double bond, and Cy, $R^1$, $R^2$, $R^3$, $R^4$, $R^5$, $R^6$, $R^{7a}$, $R^{7b}$, $R^{7c}$, X and Z are as defined in US 2006/0035841.

7) D-xylopyranosyl-substituted phenyl compounds of Formula VIII or pharmaceutically acceptable salts thereof, as described in US 2006/0009400, the disclosure of which is incorporated herein by reference in its entirety for any purpose, Formula VIII

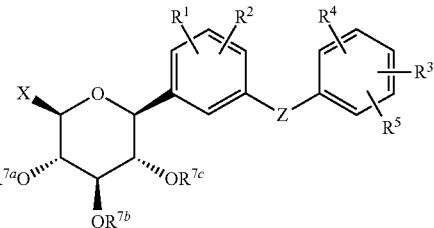

wherein $R^1$, $R^2$, $R^3$, $R^4$, $R^5$, $R^{7a}$, $R^{7b}$, $R^{7c}$, X and Z are as disclosed in US 2006/0009400.

8) D-glucopyranosyl-phenyl-substituted compounds of Formula IX or pharmaceutically acceptable salts thereof, as described in US 2006/0025349, the disclosure of which is incorporated herein by reference in its entirety for any purpose, Formula IX

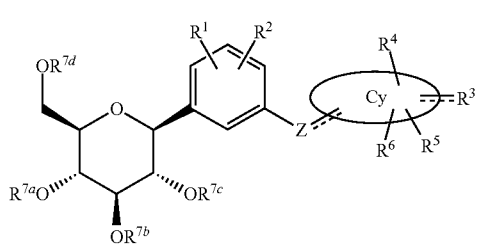

wherein $\doteq$ denotes a single or double bond, and Cy, $R^1$, $R^2$, $R^3$, $R^4$, $R^5$, $R^6$, $R^{7a}$, $R^{7b}$, $R^{7c}$, $R^{7d}$ and Z are as defined in US 2006/0025349.

9) C-glycoside derivatives of Formula X or pharmaceutically acceptable salts thereof, as described in US 2006/0122126, the disclosure of which is incorporated herein by reference in its entirety for any purpose, Formula X

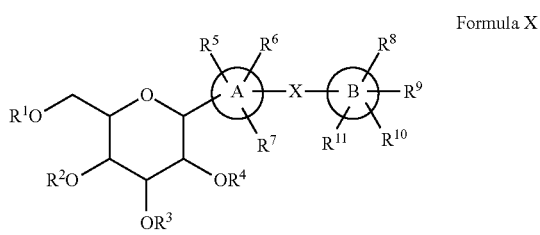

wherein $R^1$, $R^2$, $R^3$, $R^4$, $R^5$, $R^6$, $R^7$, $R^8 R^9$, $R^{10}$, $R^{11}$, X, A and B are as defined in US 2006/0122126.

10) D-xylopyranosyl-substituted phenyl compounds of Formula XI or pharmaceutically acceptable salts thereof as described in US 2006/0019948, the disclosure of which is incorporated herein by reference in its entirety for any purpose,

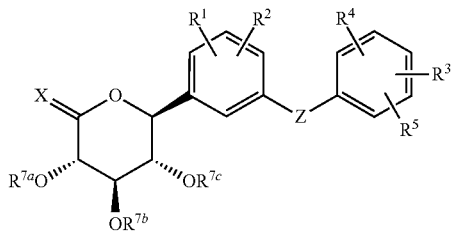

Formula XI wherein $R^1$, $R^2$, $R^3$, $R^4$, $R^5$, $R^{7a}$, $R^{7b}$, $R^{7c}$, X and Z are as defined in US 2006/0019948.

Examples of O-glucoside SGLT2 inhibitors useful in the methods of the invention include, but are not limited to, the following:

1) 5-Thio-β-D-glucopyranoside compounds of Formula XII or pharmaceutically acceptable salts or hydrates thereof, as described in US 2006/0194809, the disclosure of which is incorporated by reference in its entirety for any purpose,

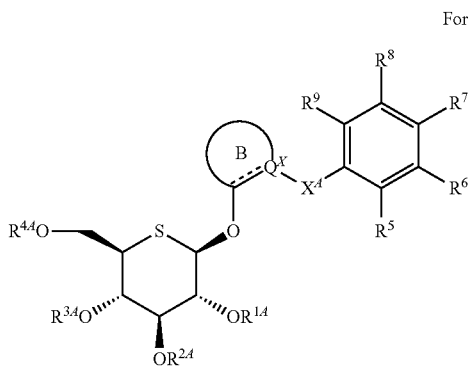

Formula XII wherein $R^{1A}$, $R^{2A}$, $R^{3A}$, $R^{4A}$, $R^5$, $R^6$, $R^7$, $R^8$, $R^9$, $Q^x$, $X^A$ and B are as defined in US 2006/0194809.

2) Glucopyranyloxybenzene derivatives of Formula XIII as described in WO 03/01180, the disclosure of which is incorporated by reference in its entirety, for any purpose,

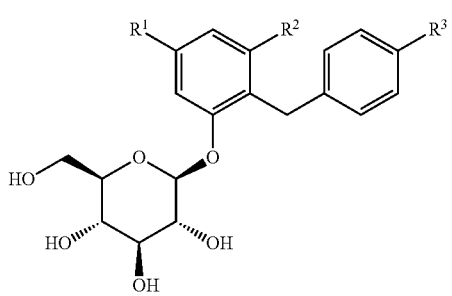

Formula XIII wherein $R^1$ represents hydrogen, hydroxyl, optionally substituted amino, cyano, carbamoyl, optionally substituted lower alkyl, optionally substituted lower alkoxy, or optionally substituted cyclic amino;

$R^2$ represents hydrogen or lower alkyl; and $R^3$ represents optionally substituted aryl, optionally substituted cycloalkyl, an optionally substituted aliphatic heterocyclic group, or an optionally substituted aromatic heterocyclic group, a pharmacologically acceptable salt of the derivative, or a prodrug of either.

3) Pyrazole derivatives of Formula XIV or XV or pharmaceutically acceptable salts thereof, as described in U.S. Pat. No. 6,908,905, the disclosure of which is incorporated herein by reference in its entirety for any purpose,

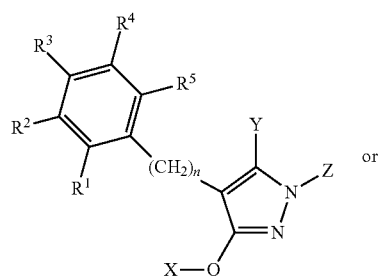

Formula XIV

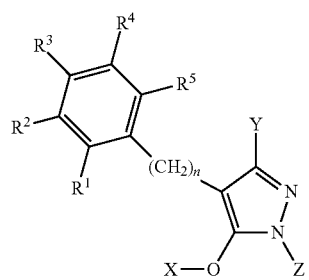

Formula XV wherein

X represents β-D-glucopyranosyl group, wherein one or more hydroxyl groups can be acylated;

Y represents a lower alkyl group or a perfluoro lower alkyl group;

Z represents a cyclic alkyl group which can have a substituent(s), a cyclic unsaturated alkyl group which can have a substituent(s), a lower alkyl group having a cyclic alkyl group which can have a substituent(s), or a lower alkyl group having a cyclic unsaturated alkyl group which can have a substituent(s);

$R^1$ to $R^5$ can be the same or different and each represent a hydrogen atom, a lower alkyl group, a perfluoro lower alkyl group, a lower alkyloxy group, a perfluoro lower alkoxyl group, a lower alkylthio group, a perfluoro lower alkylthio group, a lower alkylamino group, a halogen group, a lower alkanoyl group, an alkenyl group, a cyclic alkenyl group, an alkynyl group, a phenyl group which can have a substituent(s), or a lower alkoxycarbonyl group; and n is an integer of 0 to 3 including

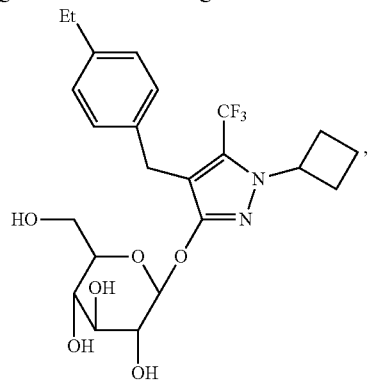

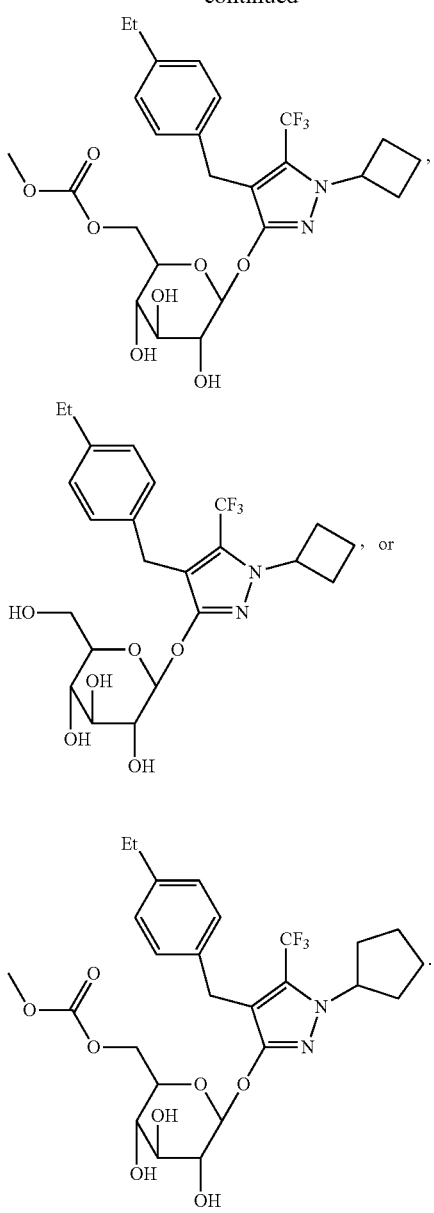

4) Pyrazole compounds of Formula XVI or XVII or pharmaceutically acceptable salts thereof, as described in U.S. Pat. No. 6,815,428, the disclosure of which is incorporated herein by reference in its entirety for any purpose, Formula XVI

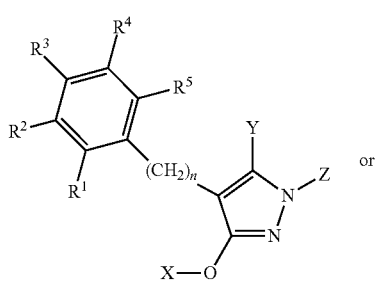

Formula XVII

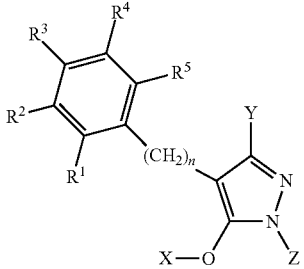

wherein
X represents a β-D-glucopyranosyl group, of which one or more hydroxyl groups can be acylated or a β-D-glucuronyl group, of which one or more hydroxyl groups can be acylated and a carboxyl group can be esterified;
Y represents a lower alkyl group or a perfluoro lower alkyl group;
Z represents a hydrogen atom, a lower alkyl group, a perfluoro lower alkyl group, an aralkyl group or a phenyl group;
$R^1$, $R^2$, $R^4$ and $R^5$ can be the same or different and each represents a hydrogen atom, a lower alkyl group, a perfluoro group, a lower alkoxy group, a fluoro lower alkoxy group, a lower alkylthio group, a perfluoro lower alkylthio group, a lower alkyl amino group, a halogen group, a lower alkanoyl group, a lower alkenyl group or a lower alkynyl group; and n represents an integer from 0 to 3,
wherein at least one of $R^1$, $R^2$, $R^4$ and $R^5$ represents a lower alkyl group having 1 to 6 carbon atoms, lower alkylthio group having 1 to 6 carbon atoms, halogen atom, lower alkoxy group lower alkenyl group or lower alkynyl group; and $R^3$ represents a lower alkyl group having a 1 to 6 carbon atoms, a lower alkylthio group having 1 to 6 carbon atoms, a halogen atom, a lower alkoxy group, a lower alkenyl group, or a lower alkynyl group.

5) O-glucosylated benzamide compounds of Formula XVIII or pharmaceutically acceptable salts thereof as described in U.S. Pat. No. 6,555,519, the disclosure of which is incorporated herein by reference in its entirety for any purpose, Formula XVIII

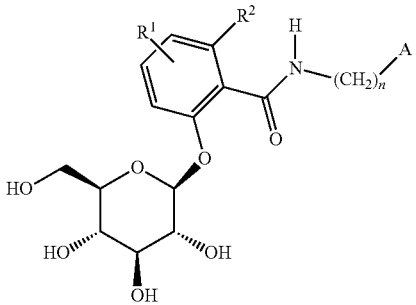

wherein
n is 0, 1 or 2;
A is

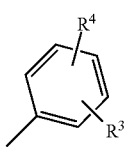

or heteroaryl which can contain 1 to 4 heteroatoms in the ring which can be selected from N, O, S, SO, and/or $SO_2$ bearing substituents $R^3$ and $R^4$;

$R^1$ is selected from hydrogen, $OR^5$, lower alkyl, aryl, arylalkyl, $NHCOR^5$, $NR^6R^{6a}$, or halogen;

$R^2$ is selected from hydrogen, OH, $OR^{5a}$, or lower alkyl;

$R^3$ an $R^4$ are the same or different and are independently selected from hydrogen, OH, $OR^{5b}$, OAryl, $OCH_2$Aryl, lower alkyl, cycloalkyl, aryl, arylalkyl, $CF_3$, $-SCF_3$, $-OCHF_2$, $-OCF_3$, halogen, $-CN$, $-CO_2R^{5c}$, $-CO_2H$, $-CONR^{6b}R^{6c}$, $-NR^{6d}R^{6e}$, $-SO_2NH_2$, $-NHCOR^{5d}$, $-NHSO_2R^{5e}-NHSO_2$Aryl, $-SR^{5f}$, $-SOR^{5g}$, $-SO_2R^{5h}$, $-SO_2$ Aryl, $-OCH_2CO_2R^{5i}$, $-OCH_2CO_2H$, $-OCH_2CONR^{6f}R^{6g}$, $-OCH_2CH_2NR^{6h}R^{6i}$, or a 5-, 6- or 7-membered heterocycle which can contain 1 to 4 heteroatoms in the ring which are N, O, S, SO, and/or $SO_2$, or $R^3$ and $R^4$ together with the carbons to which they are attached form an annelated 5-, 6- or 7-membered carbocycle or heterocycle which can contain 1 to 4 heteroatom in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$, and $R^{5i}$ are independently lower alkyl;

$R^6$, $R^{6a}$, $R^{6b}$, $R^{6c}$, $R^{6d}$, $R^{6e}$, $R^{6f}$, $R^{6g}$, $R^{6h}$, and $R^{6i}$ are the same or different and are independently selected from hydrogen, alkyl, aryl, arylalkyl or cycloalkyl.

6) O-arylglucoside compounds of Formula XIX or pharmaceutically acceptable salts thereof as described in U.S. Pat. No. 6,683,056, the disclosure of which is incorporated herein by reference in its entirety for any purpose, Formula XIX

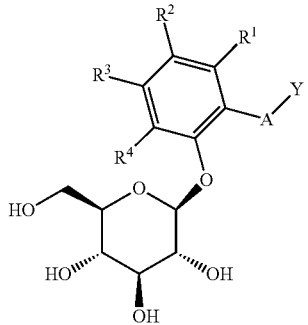

wherein when Y is

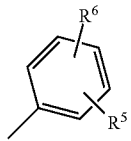

or heteroaryl;

$R^1$, $R^2$, $R^3$, and $R^4$ are the same or different and are independently selected from hydrogen, OH, $OR^7$, lower alkyl, or halogen, or two of $R^1$, $R^2$, $R^3$, and $R^4$ together with the carbons to which they are attached can form an annelated 5-, 6- or 7-membered carbocycle or heterocycle which can contain 1 to 4 heteroatoms in the ring which are N, O, S, SO, and/or $SO_2$;

$R^5$ and $R^6$ are the same or different and are independently selected from hydrogen, OH, $OR^{7a}$, $-$OAryl, $-OCH_2$Aryl, lower alkyl, cycloalkyl, Aryl, arylalkyl, $CF_3$, arylalkenyl, $-OCHF_2$, $-OCF_3$, halogen, $-CN$, $-CO_2R^{7b}$, $-CO_2H$, $COR^{8f}$, $CHOHR^{8g}$, $CH(OR^{7h})R^{8h}$, $-CONR^8R^{8a}$, $-NHCOR^{7c}$, $-NHSO_2R^{7d}$, $-NHSO_2$Aryl, $-SR^{7e}$, $-SOR^{7f}$, $-SO_2R^{7g}$, $-SO_2$Aryl, $-OCH_2CO_2R^{7i}$, $-OCH_2CO_2H$, $-OCH_2CONR^{8b}R^{8c}$, $-OCH_2CH_2NR^{8d}R^{8e}$, or a 5-, 6- or 7-membered heterocycle which can contain 1 to 4 heteroatoms in the ring which are N, O, S, SO, and/or $SO_2$, or $R^5$ and $R^6$ together with the carbons to which they are attached form an annelated 5-, 6- or 7-membered carbocycle or heterocycle which can contain 1 to 4 heteroatoms in the ring which are N, O, S, SO, and/or $SO_2$;

$R^7$, $R^{7a}$, $R^{7b}$, $R^{7c}$, $R^{7d}$, $R^{7e}$, $R^{7f}$, $R^{7g}$, $R^{7h}$, and $R^{7i}$ are independently lower alkyl;

$R^8$, $R^{8a}$, $R^{8b}$, $R^{8c}$, $R^{8d}$, $R^{8e}$, $R^{8f}$, $R^{8g}$, and $R^{8h}$ are the same or different and are independently selected from hydrogen, alkyl, aryl, arylalkyl, cycloalkyl, or together with the nitrogen to which they are attached form an annelated 5-, 6- or 7-membered heterocycle which can contain 1 to 4 heteroatoms in the ring which are N, O, S, SO, and/or $SO_2$;

A is $O(CH_2)_m$, S, $NH(CH_2)_m$, or $(CH_2)_n$ where n is 0-3 and m is 0-2.

Other O-aryl glucosides SGLT2 inhibitors which can be used in the present invention are described in the following references, all of which are incorporated herein by reference in their entireties for any purpose:

1) EP 598359 A1 (JP 035988 and U.S. Pat. No. 5,731,292), the disclosures of which are incorporated herein by reference for any purpose, discloses compounds of Formula XX, as shown:

Formula XX

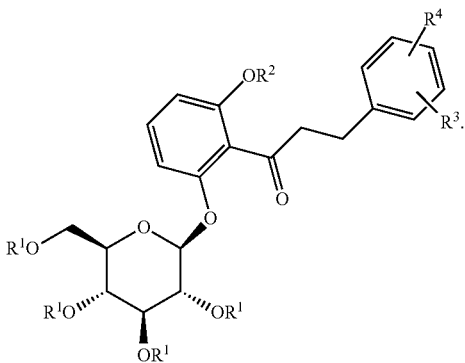

$R^1$ = H, acyl,
$R^2$ = H, Me
$R^3$ and $R^4$ as defined in EP 598359 A1

2) EP 0850948 A1 (U.S. Pat. No. 6,048,842), the disclosure of which is incorporated herein by reference in its entirety for any purpose, discloses compounds of Formula XXI, as shown:

Formula XXI

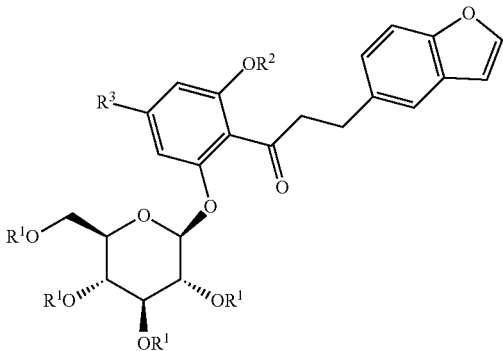

$R^1$ = H, acyl, CO(OAlkyl)
$R^2$ = H, allyl
$R^3$ = H or Me

3) JP 09188625 A, the disclosure of which is herein incorporated by reference for any purpose in its entirety, discloses compounds of Formula XXII as shown, where $R^3$ is H, ⇌ represents a single or double bond, and X=S or $CH_2$:

Formula XXII

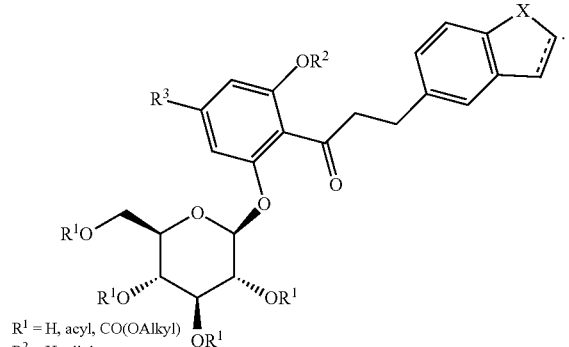

$R^1$ = H, acyl, CO(OAlkyl)
$R^2$ = H, allyl
$R^3$ = H

4) JP 09124685 A, the disclosure of which is herein incorporated by reference in its entirety for any purpose, includes derivatives of Formula XXIII as shown, where aryl group of C(O)-aryl or C(O)O-aryl is a substituted benzoic or pyridyl carboxylic acid or a urethane generated from the corresponding phenol:

Formula XXIII

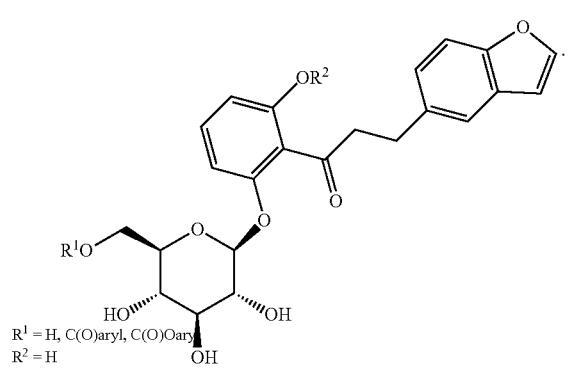

$R^1$ = H, C(O)aryl, C(O)Oaryl
$R^2$ = H

5) JP 09124684, the disclosure of which is herein incorporated by reference for any purpose in its entirety, discloses derivatives of Formula XXIV, as shown:

Formula XXIV

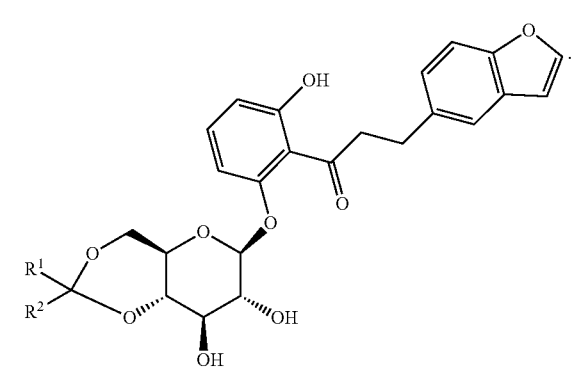

$R^1, R^2$ = H, alkyl, alkoxy, aryl or together oxo

6) EP 773226 A1 (U.S. Pat. No. 5,767,094), the disclosure of which is herein incorporated by reference in its entirety for any purpose, discloses derivatives of Formula XXV, as shown.

Formula XXV $R^1$ = alkanoyl if $R^2$ = H
$R^2$ = alkoxycarbonyl if $R^1$ = H

7) JP 08027006 A, the disclosure of which is herein incorporated by reference in its entirety for any purpose, discloses derivatives of Formula XXV as shown where various combinations of the glucose hydroxyl are acylated, similar to those disclosed in EP 598359 A1.

8) EP 684254 A1, the disclosure of which is herein incorporated by reference in its entirety for any purpose, discloses compounds of Formula XXII (shown above) similar to those described in JP 09188625 A.

Other disclosures and publications which disclose SGLT2 inhibitors that can be employed in the methods of the invention are as follows:

9) Tsujihara, K. et al., *Chem. Pharm. Bull.,* 44:1174-1180 (1996);

10) Hongu, M. et al., *Chem. Pharm. Bull.,* 46:22-33 (1998);

11) Hongu, M. et al., *Chem. Pharm. Bull.,* 46:1545-1555 (1998); and

12) Oku, A. et al., *Diabetes,* 48:1794-1800 (1999).

13) JP 10245391 (Dainippon) discloses 500 structures as hypoglycemic agents for treatment of diabetes. These are O-glucosides of hydroxylated coumarins.

In addition to the above SGLT2 inhibitors, other SGLT2 inhibitors that can be employed in the methods of the invention include those disclosed in US 2005/0233982 (Boehringer Ingelheim Corp.), US 2005/0119192 (Kissei Pharmaceutical Co.), WO 2006/035796 (Kissei Pharmaceutical Co.), JP 2006/117651 (Taisho Pharmaceutical Co.), JP 2004/4359630 (Yamanouchi Pharmaceutical Co.), WO 2006/080421 (Chugai Seiyaku Kabushiki Kaishi), US 2005/0233988 (Tanabe Seiyaku Co.), WO 2005/012321 (Tanabe Seiyaku Co.), U.S. Pat. No. 7,015,201 (Ajinomoto Co.), WO 2006/058597 (Merck Patent GmbH), WO 2006/011469 (Chugai Seiyaku Kabushiki Kaisha), US 2003/0195235 (Johnson & Johnson), and WO 2006/037537 (Boehringer Ingelheim), the disclosures of which are herein incorporated by reference in their entireties for any purpose.

Where desired, the SGLT2 inhibitor may be used in combination with one or more other anti-diabetic agents, and/or other therapeutic agents such as anti-obesity agents, anti-hyperlipidemic agents, anti-atherosclerotic agents, anti-hypertensive agents, and/or platelet aggregation inhibitors, that can be administered orally in the same dosage form, in a separate oral dosage form or by injection.

The other anti-diabetic agent that can be optionally employed in combination with the SGLT2 inhibitor according to the methods of this invention can be one or more antihyperglycemic agents including insulin secretagogues or insulin sensitizers, or other anti-diabetic agents preferably having a mechanism of action different from SGLT2 inhibition, but may be an SGLT2 inhibitor as well. The other anti-diabetic agents can include biguanides, sulfonyl ureas, glucosidase inhibitors, PPAR γ agonists such as thiazolidinediones, aP2 inhibitors, PPAR α/γ dual agonists, dipeptidyl peptidase IV (DPP4) inhibitors, and/or meglitinides, as well as insulin, glucagon-like peptide-1 (GLP-1) receptor agonists, glucokinase activators, DGAT inhibitors, CCR2 antagonists, 11-β-HSD, PTP1B inhibitors, glycogen phosphorylase inhibitors and/or glucose-6-phosphatase inhibitors.

These other anti-diabetic agents can be an oral antihyperglycemic agent preferably a biguanide such as metformin or phenformin or salts thereof, preferably metformin HCl.

Where the other anti-diabetic agent is a biguanide, the SGLT2 inhibitor is employed in a weight ratio to biguanide within the range from about 0.01:1 to about 100:1, preferably from about 0.1:1 to about 5:1.

The other anti-diabetic agent also can be preferably a sulfonyl urea such as glyburide (also known as glibenclamide), glimepiride (as disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred. These other anti-diabetic agents can be administered in the same or in separate oral dosage forms.

The SGLT2 inhibitor is preferably employed in a weight ratio to the sulfonyl urea in the range from about 0.01:1 to about 100:1, preferably from about 0.2:1 to about 10:1.

The oral anti-diabetic agent also can be a glucosidase inhibitor such as acarbose (disclosed in U.S. Pat. No. 4,904,769) or miglitol (disclosed in U.S. Pat. No. 4,639,436), and can be administered in the same or separate oral dosage forms.

The SGLT2 inhibitor is preferably employed in a weight ratio to the glucosidase inhibitor within the range from about 0.01:1 to about 100:1, preferably from about 0.5:1 to about 50:1.

The SGLT2 inhibitor also can be employed in combination with a PPAR γ agonist such as a thiazolidinedione oral anti-diabetic agent or other insulin sensitizers (which has an insulin sensitivity effect in NIDDM patients) such as troglitazone (Warner-Lambert's REZULIN®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer), isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably pioglitazone and rosiglitazone.

The SGLT2 inhibitor preferably is employed in a weight ratio to the thiazolidinedione in an amount within the range from about 0.01:1 to about 100:1, preferably from about 0.2:1 to about 10:1.

In said embodiments, the sulfonyl urea and thiazolidinedione are administered in amounts of less than about 150 mg oral anti-diabetic agent and can be incorporated in a single tablet with the SGLT2 inhibitor.

The SGLT2 inhibitor also can be employed in combination with an antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylen) and LY-315902 (Lilly). These anti-diabetic agents can be administered via injection, intranasally, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) can be employed in formulations as described above and in amounts and dosing as indicated in the *Physicians' Desk Reference* (PDR) or *Remington's Pharmaceutical Sciences* (Mack Publishing Co., Easton, Pa.).

Where present, metformin or salt thereof is preferably employed in amounts within the range from about 500 to about 2000 mg per day, and can be administered in single or divided doses one to four times daily. Metformin or a salt thereof can be employed in combination with a thiazolidinedione such as pioglitazone or rosiglitazone, together with the SGLT2 inhibitor.

Where present, the thiazolidinedione anti-diabetic agent, such as rosiglitazone or pioglitazone, is preferably employed in amounts within the range from about 0.01 to about 150 mg/day, and can be administered in single or divided doses one to four times per day.

Where present insulin may be employed in formulations, amounts and dosing as indicated by the *Physicians' Desk Reference* (PDR) or *Remington's Pharmaceutical Sciences*.

Where present GLP-1 peptides preferably can be administered in oral buccal formulations, by nasal administration or parenterally as described in U.S. Pat. No. 5,346,701 (TheraTech), U.S. Pat Nos. 5,614,492 and 5,631,224, each of which are incorporated herein by reference in their respective entireties.

The other anti-diabetic agent also can be a PPAR α/γ dual agonist such as AR-HO39242 (Astra/Zeneca), GW-409544 (Glaxo-Wellcome), KRP297 (Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", *Diabetes*, 47:1841-1847 (1998), and in U.S. Pat. No. 6,414,002, the disclosure of each of which is incorporated herein by reference in their respective entireties, employing dosages as set out therein, which compounds designated as preferred are preferred for use herein.

The other anti-diabetic agent may be a glucokinase activator as disclosed in WO 2008/005964 and/or a DGAT-1 inhibitor as disclosed in US2008/0090876A1.

The other anti-diabetic agent may be an aP2 inhibitor such as disclosed in U.S. Pat. No. 6,548,529 employing dosages as set out therein. Preferred are the compounds designated as preferred in the above application.

The other anti-diabetic agent may be a DPP4 inhibitor such as disclosed in U.S. Pat. No. 6,395,767, WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., *Biochemistry*, 38 (36): 11597-11603 (1999), TSL-225 (tryptophyl-1,2,3,4-tetrahydroisoquinoline-3-carboxylic acid (disclosed by Yamada et al., *Bioorg. & Med. Chem. Lett.*, 8:1537-1540 (1998); 2-cyanopyrrolidides and 4-cyanopyrrolidides as disclosed by Ashworth et al, *Bioorg. & Med. Chem. Lett.*, 6 (22):1163-1166 and 2745-2748 (1996), with saxagliptin, vildagliptin and sitagliptin being preferred, employing dosages as set out in the above references.

The meglitinide that can be optionally employed in combination with SGLT2 of the invention can be repaglinide, nateglinide (Novartis) or KAD1229 (PF/Kissei), with repaglinide being preferred.

The SGLT2 inhibitor is preferably employed in a weight ratio to the meglitinide, PPAR γ agonist, PPAR α/γ dual agonist, aP2 inhibitor or DPP4 inhibitor within the range from about 0.01:1 to about 100:1, preferably from about 0.2:1 to about 10:1.

The anti-obesity agents that can be optionally employed with the SGLT2 inhibitor in the methods of the invention include one or more of the following: beta 3 adrenergic agonist(s), lipase inhibitor(s), serotonin (and dopamine) reuptake inhibitor(s), thyroid receptor beta drug(s), MCH-1 receptor antagonist(s), agonist(s) of the 5-HT2c receptor, anorectic agent(s), Neuropeptide Y (NPY) antagonist(s), such as an NPY5 antagonist and an NPY2 antagonist, Leptin analog(s), MC4 receptor agonist(s), and/or antagonist(s) of the cannabinoid receptor.

Examples of suitable beta 3 adrenergic agonists that can be optionally administered in combination with the SGLT2 inhibitor include, but are not limited to, AJ9677 (Takeda/Dainippon), SB-418790, L750355 (Merck), CP331648 (Pfizer), and other known beta 3 agonists as disclosed in U.S. Pat. Nos. 5,541,204, 5,770,615, 5,491,134, 5,776,983 and 5,488,064. In one embodiment, the beta 3 adrenergic agonist is selected from the group consisting of AJ9677, L750355, and CP331648.

Examples of suitable lipase inhibitors that can be optionally administered in combination with the SGLT2 inhibitor include, but are not limited to, orlistat and ATL-962 (Alizyme). In one embodiment, the lipase inhibitor is orlistat.

Examples of suitable serotonin (and dopamine) reuptake inhibitors that can be optionally administered in combination with the SGLT2 inhibitor include, but are not limited to, sibutramine, topiramate (Johnson & Johnson), AXOKINE® (Regeneron), dexphenfluramine, and tetrahydrolipostatin. In one embodiment, the serotonin (and dopamine) reuptake inhibitor is selected from the group consisting of sibutramine and topiramate.

Examples of suitable thyroid receptor beta compounds that can be optionally administered in combination with the SGLT2 inhibitor include, but are not limited to, thyroid receptor ligands as disclosed in WO 97/21993 (U. Cal SF), WO 99/00353 (KaroBio) and WO 00/039077 (KaroBio). In one embodiment, the thyroid receptor beta compound is selected from the compounds disclosed in WO 99/00353 and WO 00/039077.

Examples of suitable anorectic agents that can be optionally administered in combination with the SGLT2 inhibitor include, but are not limited to, dexamphetamine, phentermine, phenylpropanolamine and mazindol. In one embodiment, the anorectic agent is dexamphetamine.

The various anti-obesity agents described above can be employed in the same dosage form with the SGLT2 inhibitor or in different dosage forms, in dosages and regimens as generally known in the art or in the *Physicians' Desk Reference*.

In accordance with the methods of the invention, the SGLT2 inhibitor may be employed in combination with antihyperlipidemic (or hypolipidemic) agents, or agents used to treat arteriosclerosis. An example of an hypolipidemic agent or agent used to treat atherosclerosis would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, and quinoline and pyridine derivatives disclosed in U.S. Pat. Nos. 5,506,219 and 5,691,322, rosuvastatin calcium and related compounds. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog $\underline{A}$ and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987) and cyclopropanes reported by Capson, T. L., Ph.D. dissertation, June, 1987, Dept. Med. Chem. U of Utah, Abstract, Table of Contents, pp. 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX®, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in Drugs of the Future, 24:9-15 (1999) (Avasimibe); Nicolosi et al., "The ACAT inhibitor, Cl-1011 is effective in the prevention and regression of aortic fatty streak area in hamsters", Atherosclerosis (Shannon, Irel.), 137 (1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", Cardiovasc. Drug Rev., 16 (1):16-30 (1998); Smith, C. et al., "RP 73163: a bioavailable alkylsulfinyl-diphenylimidazole ACAT inhibitor", Bioorg. Med. Chem. Lett., 6 (1):47-50 (1996); Krause, B. R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R. R. et al., eds., pp. 173-198 (1995); Sliskovic et al., "ACAT inhibitors: potential anti-atherosclerotic agents", Curr. Med. Chem., 1 (3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Chemtracts: Org. Chem., 8 (6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis, 115:45-63 (1995) and J. Med. Chem., 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in Drugs of the Future, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin, rosuvastatin, and ezetimibe as well as niacin and/or cholestagel.

The SGLT2 inhibitor may be employed in combination with one or more anti-hypertensive agents in the methods of the present invention. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

The SGLT2 inhibitor may also be used in combination with one or more antithrombotic or anticoagulant drugs in the methods of the present invention such as thrombin inhibitors, platelet aggregation inhibitors such as clopidogrel, ticlopidine, prasugrel (Eli Lilly), PAI-1 inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, aspirin, ifetroban, picotamide, ketanserin and the like.

The aforementioned patents and patent applications are incorporated herein by reference.

The above other anti-diabetic agents and other therapeutic agents, when employed in combination with the SGLT2 inhibitor in the method of the invention can be used, for example, in those amounts indicated in the Physicians' Desk Reference (PDR) or Remington's Pharmaceutical Sciences as in the patents or applications set out above or patents or applications which disclose these agents or as otherwise determined by one of ordinary skill in the art.

In carrying out the methods of the invention, a pharmaceutical composition is employed where the pharmaceutical composition comprises an SGLT2 inhibitor, with or without one or more anti-diabetic agents and/or one or more therapeutic agents, and a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, and the like by an oral route, for example, in the form of tablets, capsules, granules or powders, or they can be administered by a parenteral route in the form of injectable preparations, or they can be administered intranasally or in transdermal patches. The dose for adults may be from 0.5 to 350 mg per day, preferably between 1 and 200 mg per day, more preferably 2.5 to 100 mg per day, which can be administered in a single dose or in the form of individual doses from 1-4 times per day.

In carrying out the method of the invention, a pharmaceutical composition is employed comprising an SGLT2 inhibitor and one or more anti-diabetic agents and/or one or more other therapeutic agents (as described above), in association with a pharmaceutical carrier, vehicle or diluent. The pharmaceutical composition can be formulated employing conventional solid or liquid vehicles, diluents, and pharmaceutical additives as appropriate for the mode of desired administration. The pharmaceutical compositions can be administered to mammalian species, including humans, monkeys, dogs, and other mammals by a variety of routes including, for example, orally, in the form of tablets, capsules, granules, powders, and the like, parenterally, in the form of injectable preparations, intranasally, rectally, and transdermally, in the form of patches, for example.

The amount of drug required for therapeutic effect varies with the agent chosen, the nature and severity of the condition, and the mammal undergoing treatment, and is ultimately at the discretion of the physician. Furthermore, the optimal quantity and spacing of individual dosages of a drug is determined by the nature and extent of the weight loss desired, the form, route, and site of administration, the particular mammal or patient being treated. The dose administered is adjusted according to the age, weight, and condition of the mammal or patient, as well as the route of administration, dosage form and regimen, and the desired result. Such dosages and forms of administration is determined using conventional techniques. It is also appreciated that the optimal course of treatment, that is, the number of doses given, can be ascertained by those skilled in the art using conventional course of treatment determination tests.

The above dosage forms can also include the necessary physiologically acceptable carrier material, excipient, lubricant, buffer, antibacterial, bulking agent (such as mannitol), and the like.

The various formulations or compositions employed in the methods of the invention can optionally include one or more fillers or excipients in an amount within the range of from about 0% to about 90% by weight and preferably from about 1% to about 80% by weight. Examples of suitable excipients include, but are not limited to, lactose, sugar, corn starch, modified corn starch, mannitol, sorbitol, inorganic salts, such as calcium carbonate, and cellulose derivatives, such as wood cellulose and microcrystalline cellulose.

One or more binders can be present in addition to or in lieu of the fillers in an amount within the range of from about 0% to about 35%. In one embodiment, the binders are present in an amount of from about 0.5% to about 30% by weight of the composition. Examples of suitable binders include polyvinylpyrrolidone (molecular weight ranging from about 5000 to about 80,000 and preferably about 40,000), lactose, starches, such as corn starch, modified corn starch, sugars, gum acacia and the like, as well as a wax binder in finely powdered form (less than 500 microns), such as carnauba wax, paraffin, spermaceti, polyethylenes and microcrystalline wax.

Where the composition is in the form of a tablet, it can include one or more tabletting lubricants in an amount within the range of from about 0.2% to about 8% by weight of composition. In one embodiment, the lubricant(s) is in an amount within the range of from about 0.5% to about 2% by weight of the composition. Examples of suitable lubricants include, but are not limited to, magnesium stearate, stearic acid, palmitic acid, calcium stearate, talc, carnauba wax, and the like. Other ingredients can optionally be present, including, for example, preservatives, stabilizers, colorants, antiadherents and silica flow conditioners or glidants, such as Syloid brand silicon dioxide.

Tablets employed in the methods of the invention can also optionally include a coating layer which can comprise from about 0% to about 15% by weight of the tablet composition. The coating layer can comprise any conventional coating formulations that can include, for example, one or more film-formers or binders and/or one or more plasticizers. Examples of suitable film-formers or binders include, but are not limited to, hydrophilic polymers, such as hydroxypropylmethylcellulose, hydrophobic polymers, such as methacrylic acid esters, neutral polymers, ethyl cellulose, cellulose acetate, polyvinyl alcohol-maleic anhydride copolymers, β-pinene polymers, glyceryl esters of wood resins and the like. Examples of suitable plasticizers include, but are not limited to, triethyl citrate, diethyl phthalate, propylene glycol, glycerin, butyl phthalate, castor oil and the like. Both core tablets as well as coating formulations can contain aluminum lakes to provide color.

The film formers are applied from a solvent system containing one or more solvents including water, alcohols such as methyl alcohol, ethyl alcohol and isopropyl alcohol, ketones such as acetone and ethylmethyl ketone, chlorinated hydrocarbons such as methylene chloride, dichloroethane, and 1,1,1-trichloroethane.

Where a color is employed, the color can be applied together with the film former, plasticizer, and solvent compositions.

Examples of formulations or compositions containing an SGLT2 inhibitor for use in the methods of the invention and a process for preparing such formulations are set out in U.S. application Ser. No. 60/896,286 filed Mar. 22, 2007, the disclosure of which is incorporated herein by reference in its entirety for any purpose.

Examples of certain specific embodiments of tablet and capsule formulations employed in the methods of the invention are set out below.

TABLE I

Tablet and Capsule Formulations

| Material | Possible Range % by weight of tablet or capsule fill | More Specific Range % by weight of tablet or capsule fill |
|---|---|---|
| Dapagliflozin or dapagliflozin-PGS | 0.1 to 70% | 0.1 to 30% |
| Bulking Agent/binder | 1 to 95% | 10 to 85% |
| Anhydrous Lactose | 0 to 95% | 20 to 75% |
| Microcrystalline cellulose | 0 to 95% | 20 to 75% |
| Pregelatinized starch | 0 to 95% | 10 to 75% |
| Disintegrant | 0 to 20% | 0.25 to 10% |
| Croscarmellose sodium | 0 to 20% | 2 to 10% |
| Crospovidone | 0 to 12% | 4 to 10% |
| Sodium Starch glycolate | 0 to 20% | 2 to 10% |
| Lubricant | 0.1 to 5% | 0.2 to 2% |
| Magnesium Stearate | 0.1 to 5% | 0.2 to 2% |
| Anti adherent/glidant | 0 to 10% | 1 to 10% more preferably 1 to 4% |
| Talc, silicon dioxide | | |

TABLE I-continued

Tablet and Capsule Formulations

| Outer Protective Coating Layer | % by weight of tablet or capsule fill | % by weight of tablet or capsule fill |
|---|---|---|
| Coating polymer, and optional plasticizer(s), glidant(s), anti-tacking agent(s), and colorant(s) | 0.5 to 50% | 1 to 5% |

TABLE II

Granulation Composition (% w/w) for Tablets and Capsules

| Ingredient | Range % by weight | More Specific Range % by weight | More Specific Formulation % w/w |
|---|---|---|---|
| Dapagliflozin or Dapagliflozin-PGS | 0.1-40 | 5-15 | 9.84 |
| Microcrystalline Cellulose | q.s. | q.s. | 63.91 |
| Lactose Anhydrous | 0-50 | 10-30 | 20 |
| Crospovidone XL-10 | 1-15 | 3-10 | 4 |
| Silicon Dioxide | 0-6 | 0.5-4 | 1.5 |
| Magnesium Stearate | 0.0-4.0 | 0.5-2.0 | 0.75 | q.s. refers to the quantity sufficient to make the granulation composition 100% w/w.

A film coating for capsules or tablets of Table II comprises, for example, polyvinyl alcohol (PVA), titanium dioxide, polyethylene glycol 3350, talc, and colorant.

Tablets or capsules of various strengths (0.1-50 mg) can be prepared using different weights of the stock granulations described herein.

The pharmaceutical formulation for use in the method of the invention in the form of a tablet can be obtained by a process comprising the steps of:
  a) mixing the inactive ingredients with the SGLT2 inhibitor (for example, dapagliflozin-PGS);
  b) formulating granules;
  c) drying and/or screening the granules;
  d) blending the granules; and
  e) tabletting the blend obtained in (d) into tablets.

In one embodiment, step a) of the process employs impact blending or milling and/or sizing equipment. In one embodiment, the granules in step b) of the process are formulated by dry granulation, wet granulation, or direct compression. In one embodiment, the granules are formulated by dry granulation. In one embodiment, the granules in step d) of the process are blended with a tabletting aid or a lubricant and filler.

The pharmaceutical formulation in the form of a capsule can be obtained by a process comprising the steps of:
  a) mixing the inactive ingredients with the medicament using a combination of blending and milling processes;
  b) formulating granules;
  c) drying and/or screening the granules; and
  d) loading the granules into capsules.

In one embodiment, step a) of the process employs impact milling or blending and/or sizing equipment. In one embodiment, the granules in step b) of the process are formulated by dry granulation, wet granulation, or direct compression. In one embodiment, the granules are formulated by dry granulation.

The activity of dapagliflozin can be determined using, for example, using the assay system described below or any appropriate assay system known in the art. The mRNA sequence for human SGLT2 (GENBANK® No. M95549) is cloned by reverse-transcription and amplification from human kidney mRNA, using standard molecular biology techniques. The cDNA sequence is stably transfected into CHO cells, and clones are assayed for SGLT2 activity essentially as described in Ryan et al., "HK-2: an immortalized proximal tubule epithelial cell line from normal adult human kidney", *Kidney International*, 45:48-57 (1994). Evaluation of inhibition of SGLT2 activity in a clonally selected cell line is performed essentially as described in Ryan et al. (1994), with the following modifications. Cells are grown in 96-well plates for 2-4 days to 75,000 or 30,000 cells per well in F-12 nutrient mixture (Ham's F-12), 10% fetal bovine serum, 300 ug/ml GENETICIN® and penicillin-streptomycin. At confluence, the cells are washed twice with 10 mM Hepes/Tris, pH 7.4, 137 mM N-methyl-D-glucamine, 5.4 mM KCl, 2.8 mM $CaCl_2$, 1.2 mM $MgSO_4$. Cells are then incubated with 10 µM [$^{14}C$]AMG, and 10 µM inhibitor (final DMSO=0.5%) in 10 mM Hepes/Tris, pH 7.4, 137 mM NaCl, 5.4 mM KCl, 2.8 mM $CaCl_2$, 1.2 mM $MgSO_4$ at 37° C. for 1.5 hours. Uptake assays are quenched with ice cold 1×PBS containing 0.5 mM phlorizin, and cells are then lysed with 0.1% NaOH. After addition of MicroScint scintillation fluid, the cells are allowed to shake for 1 hour, and then [$^{14}C$]AMG (glucose analog α-methyl-D-glucopyranoside) is quantitated on a TOPCOUNT® scintillation counter. Controls are performed with and without NaCl. For determination of $EC_{50}$ values, 10 inhibitor concentrations (dapagliflozin) are used over 2 log intervals in the appropriate response range, and triplicate plates are averaged across plates.

While this invention has been particularly shown and described with references to preferred embodiments thereof, it will be understood by those skilled in the art that various changes in form and details may be made therein without departing from the scope of the invention encompassed by the appended claims. It will also be clear that the invention may be practiced otherwise than as particularly described in the foregoing description and examples. Numerous modifications and variations of the present invention are possible in light of the above teachings and, therefore, are within the scope of the appended claims.

The following examples are provided to describe the invention in further detail. These examples, which set forth the best mode presently contemplated for carrying out the invention, are intended to illustrate and not to limit the invention.

EXAMPLES

The following working Examples are illustrative of the present invention. All temperatures are expressed in degrees Centigrade unless otherwise indicated.

Capsules containing the SGLT2 inhibitor dapagliflozin or dapagliflozin-PGS were prepared in strengths of 2.5 mg (Example 1), 10 mg (Example 2) and 100 mg (Example 3) (as the non-solvated form) as two-piece, gray opaque size #0 (2.5 mg and 10 mg) and size #00 (for 100 mg) capsule shell.

Example 1

Preparation of Dapagliflozin/Dapagliflozin-PGS Capsule, 2.5 mg

A 25.0 mg of stock granulation was prepared containing 10% dapagliflozin or dapagliflozin-PGS filled in gray, opaque, size #0 capsule shell.

A. Stock Granulation Composition

| Ingredient | Amount (% w/w) |
|---|---|
| Dapagliflozin (or equivalent amount of dapagliflozin propylene glycol hydrate) | 10.0 |
| Pregelatinized Starch | 15.0 |
| Microcrystalline Cellulose | 68.75 |
| Sodium Starch Glycolate | 3.0 |
| Silicon Dioxide | 2.0 |
| Magnesium Stearate | 1.25 |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The preferred amount of magnesium stearate is 1.25% (w/w). A useful range is 1.25-1.50% (w/w).

The stock granulation of Part A and the Example 1 capsules were prepared according to the following procedures.

B. Example 1 Stock Granulation Procedure
1. Screen dapagliflozin or dapagliflozin-PGS.
2. Screen silicon dioxide.
3. Mix silicon dioxide with dapagliflozin or dapagliflozin-PGS in a suitable blender.
4. Screen pregelatinized starch and microcrystalline cellulose, if necessary.
5. Add ingredients from Step 4 to a suitable blender.
6. Add mixture from Step 3 to the blend from Step 5, and mix.
7. Screen sodium starch glycolate.
8. Add ingredient from Step 7 to the blend from Step 6, and mix.
9. Screen the blend from Step 8, and mix.
10. Screen portion of magnesium stearate.
11. Add ingredient from Step 10 to the blend from Step 9, and mix.
12. Densify the blend from Step 11.
13. Reduce the densified blend Step 12.
14. Screen the remaining portion of magnesium stearate.
15. Add ingredient from Step 14 to the granulation from Step 13, and mix.

C. Example 1 Product: Dapagliflozin/Dapagliflozin-PGS Capsule, 2.5 mg
1. Fill empty capsule shells with sufficient Example 1 Part A stock granulation for capsules (10.0%) w/w (as the non-solvated form), to provide 2.5 mg capsules.
2. De-dust the capsules.

Example 2

Preparation of Dapagliflozin/Dapagliflozin-PGS Capsule, 10 mg

A. Stock Granulation Composition
Stock granulation composition was prepared as described in Example 1A.

B. Example 2 Stock Granulation Procedure
Stock granulation procedure was performed as described in Example 1B.

C. Example 2 Product: Dapagliflozin/Dapagliflozin-PGS Capsule, 10 mg
1. Fill empty capsule shells with Example 1 Part A stock granulation for capsules (10.0% w/w as the non-solvated form), to provide 10 mg capsules.
2. De-dust the capsules.
3. Weight sort the capsules.

Example 3

Preparation of Dapagliflozin/Dapagliflozin-PGS Capsule, 100 mg

Composition: 438.6 mg of dapagliflozin (Example 3 Part A) Stock Granulation for Capsules (22.8% w/w), filled in Gray, Opaque, Size #0 Capsule Shell was prepared.

A. Stock Granulation Composition

| Ingredient | Amount (% w/w) |
|---|---|
| Dapagliflozin (or equivalent amount of dapagliflozin propylene glycol hydrate) | 22.8 |
| Pregelatinized Starch | 15.0 |
| Microcrystalline Cellulose | 55.95 |
| Sodium Starch Glycolate | 3.0 |
| Silicon Dioxide | 2.0 |
| Magnesium Stearate | 1.25 |

The amount of dapagliflozin is theoretically equivalent to 81.29% of dapagliflozin PG hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The preferred amount of magnesium stearate is 1.25% (w/w). A useful range is 1.25-1.50% (w/w).

The stock granulation of Part 3A and the Example 3 capsules were prepared according to the following procedures.

B. Stock Granulation Procedure
1. Screen silicon dioxide.
2. Mix silicon dioxide with dapagliflozin or dapagliflozin-PGS in a suitable blender.
3. Screen the blend from Step 2, and mix again.
4. Screen pregelatinized starch and microcrystalline cellulose, if necessary.
5. Add ingredients form Step 4 to the blend from Step 3, and mix.
6. Screen sodium starch glycolate.
7. Add ingredient from Step 6 to the blend from Step 5, and mix.
8. Screen a portion of magnesium stearate.
9. Add ingredient from Step 8 to the blend from Step 7, and mix.
10. Densify the blend from Step 9.
11. Reduce the densified blend from Step 10.
12. Screen the remaining portion of magnesium stearate.
13. Add ingredient from Step 12 to the granulation from Step 11, and mix.

C. Example 3 Product: Dapagliflozin/Dapagliflozin-PGS Capsule, 100 mg
1. Fill empty capsule shells with Example 3 stock granulation for capsules (22.8% w/w as the non-solvated form).
2. De-dust the capsules.
3. Weight sort the capsules.

The formed capsules of Example 1 (2.5 mg), Example 2 (10 mg), and Example 3 (100 mg) are used in treating type 2 diabetes.

Example 4

Preparation of Dapagliflozin/Dapagliflozin-PGS Tablet, 2.5 mg

Tablets containing the SGLT2 inhibitor of structure Ia (dapagliflozin (S)-propylene glycol hydrate) were prepared in strengths of 2.5 mg (Example 4), 10 mg (Example 5) and 50 mg (Example 6) as described below.

Product: Dapagliflozin/Dapagliflozin-PGS Tablet, 2.5 mg

A. Tablet Composition

| Ingredient | Amount |
| --- | --- |
| Dapagliflozin propylene glycol hydrate (or equivalent amount of dapagliflozin) | 3.08 mg |
| Microcrystalline Cellulose | 67.11 mg |
| Anhydrous Lactose | 25.00 mg |
| Crospovidone | 8.75 mg |
| Croscarmellose Sodium | 3.75 mg |
| Talc | 12.50 mg |
| Silicon Dioxide | 2.88 mg |
| Magnesium Stearate | 1.94 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 1.94 mg. An acceptable range is about 1.55 to about 2.33 mg.

The stock granulation of Part 4A and the Example 4 tablets were prepared according to the following procedures.

B. Stock Granulation Procedure

1. Deaggregate dapagliflozin propylene glycol hydrate and magnesium stearate separately using a suitable screen.

2. Mix dapagliflozin propylene glycol hydrate with a portion of microcrystalline cellulose in a suitable mixer; pass through a mill; and transfer it into a suitable blender.

3. "Dry Rinse" the mixer used for mixing Step 2 with a portion of microcrystalline cellulose.

4. Add the blend from Step 3 to the blend from Step 2.

5. Mix the mixture from Step 4 with remaining microcrystalline cellulose, portion of crospovidone, portion of croscarmellose sodium, portion of silicon dioxide and Anhydrous Lactose.

6. Add talc and intragranular magnesium stearate to the mixture from Step 5 and mix.

7. Compact the powder blend from Step 6.

8. Reduce compact from Step 7 to form granules.

9. Mix the granules from Step 8 with remaining amounts of crospovidone, croscarmellose sodium and silicon dioxide.

10. Mix the granules from Step 9 with remaining amount of magnesium stearate.

C. Example 4 Product: Dapagliflozin/Dapagliflozin-PGS Tablet, 2.5 mg

1. Setup the tabletting equipment.

2. Compress the Example 4 stock granulation into tablets.

Example 5

Preparation of Dapagliflozin/Dapagliflozin-PGS Tablet, 10 mg

Product: Dapagliflozin/Dapagliflozin-PGS Tablet, 10 mg

A. Tablet Composition

| Ingredient | Amount |
| --- | --- |
| Dapagliflozin propylene glycol hydrate (or equivalent amount of dapagliflozin) | 12.30 mg |
| Microcrystalline Cellulose | 57.89 mg |
| Anhydrous Lactose | 25.00 mg |
| Crospovidone | 8.75 mg |
| Croscarmellose Sodium | 3.75 mg |
| Talc | 12.50 mg |
| Silicon Dioxide | 2.88 mg |
| Magnesium Stearate | 1.94 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 1.94 mg. An acceptable range is about 1.55 to about 2.33 mg.

The stock granulation of Part 5A and the Example 5 tablets were prepared according to the following procedures.

B. Stock Granulation Procedure

1. Deaggregate dapagliflozin propylene glycol hydrate and magnesium stearate separately using a suitable screen.

2. Mix microcrystalline cellulose, dapagliflozin propylene glycol hydrate, portion of crospovidone, portion of croscarmellose sodium, portion of silicon dioxide and anhydrous lactose in a suitable blender.

3. Add talc and intragranular magnesium stearate to the mixture from Step 2 and mix in a suitable blender.

4. Compact the powder blend from Step 3.

5. Reduce compact from Step 4 to form granules.

6. Mix the granules from Step 5 with remaining amounts of crospovidone, croscarmellose sodium and silicon dioxide.

7. Mix the granules from Step 6 with remaining amount of magnesium stearate.

C. Example 5 Product: Dapagliflozin/Dapagliflozin-PGS Tablet, 10 mg

1. Setup the tabletting equipment.

2. Compress the Example 5 stock granulation into tablets.

Example 6

Preparation of Dapagliflozin/Dapagliflozin-PGS Tablet, 50 mg

Product: Dapagliflozin/Dapagliflozin-PGS Tablet, 50 mg

A. Tablet Composition

| Ingredient | Amount |
| --- | --- |
| Dapagliflozin propylene glycol hydrate (or equivalent amount of dapagliflozin) | 61.66 mg |
| Microcrystalline Cellulose | 114.09 mg |
| Anhydrous Lactose | 62.60 mg |
| Crospovidone | 21.91 mg |
| Croscarmellose Sodium | 9.39 mg |
| Talc | 31.30 mg |
| Silicon Dioxide | 7.20 mg |
| Magnesium Stearate | 4.85 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 4.85 mg. An acceptable range is about 3.76 to about 5.95 mg.

The stock granulation of Part 6A and the Example 6 tablets were prepared according to the following procedures.

B. Stock Granulation Procedure
1. Mix dapagliflozin propylene glycol hydrate, microcrystalline cellulose, anhydrous lactose, crospovidone, croscarmellose sodium, talc and silicon dioxide in a suitable blender.
2. Pass the mixture from Step 1 through a suitable mill.
3. Determine the yield from Step 1 and calculate the amount of magnesium stearate required.
4. Mix the mixture from Step 2 in a suitable blender.
5. Mix the mixture from Step 4 with magnesium stearate.
6. Dry granulate the powder blend from Step 5.
7. Size the granulation from Step 6.
8. Determine the yield based on Step 7.
9. Mix the granules from Step 8 with remaining amount of crospovidone, croscarmellose sodium and silicon dioxide.
10. Mix the granules from Step 9 with remaining amount of magnesium stearate.

C. Example 6 Product: Dapagliflozin/Dapagliflozin-PGS Tablet, 50 mg
1. Setup the tabletting equipment.
2. Compress the Example 6 stock granulation into tablets.

The so-formed tablets of Example 4 (2.5 mg), Example 5 (10 mg) and Example 6 (50 mg) are used to treat type 2 diabetes.

Example 7

Treatment of Type 2 Diabetes with Dapagliflozin

As type 2 diabetes (T2DM) progression occurs, many diabetic patients require combinations of insulin with oral antidiabetic agents (OADs). Unfortunately, effectiveness of these treatments is often limited by progressive weight gain, insulin resistance and hypoglycemia. Dapagliflozin selectively inhibits glucose reabsorption in the proximal tubule of the kidney, and thus can be employed as an insulin-independent therapy.

A pilot study was designed to determine if dapagliflozin is effective in lowering blood glucose in patients with T2DM who have not responded well to insulin combined with oral therapies that act through insulin-dependent mechanisms. For this proof of concept trial, dapagliflozin was administered for 12 weeks to patients with insulin resistance who were poorly controlled with exogenous insulin plus metformin and/or a TZD. Patients were assessed for changes in glycated hemoglobin ($HbA_{1c}$), fasting plasma glucose (FPG), postprandial glucose (PPG), and total body weight, and monitored for safety and hypoglycemic episodes.

Methods

Study Design

This was a randomized, single- and double-blind, three-arm parallel group, placebo-controlled trial to determine if dapagliflozin effectively lowers hyperglycemia in highly insulin-resistant T2DM patients poorly controlled with insulin plus metformin and/or thiazolidinediones. The trial consisted of a qualification period of 10 to 21 days, a treatment phase of 12 weeks, and a follow-up phase of 4 weeks. During qualification and until day 1, patients maintained their stable dose of open-label OADs, as well as their stable dose of prescribed insulin.

The treatment phase utilized an adaptive trial design with two cohorts: Cohort 1, the insulin dose-setting group; and Cohort 2, the main experimental group. The purpose of Cohort 1 was to determine the ideal starting dose of insulin least likely to cause hypoglycemia when dapagliflozin would be added. In Cohort 1, four patients were assigned to 20 mg single-blind dapagliflozin on day 1 after having their insulin dose decreased by 50%, the greatest decrement possible in this adaptive design. These patients underwent 48-hour continuous blood glucose monitoring (CGM) during the first week of treatment. Pursuant to the protocol, if at least one patient recorded a CGM value ≤100 mg/dL, confirmed by self-monitoring of blood glucose (SMBG), the total daily insulin dose for patients in Cohort 2 would be set at 50% of their usual dose that is, at an average of 52 to 54 units of insulin daily, and lesser dose reductions of insulin would not be tested. At least one patient in Cohort 1 met this condition with the 50% insulin reduction, resulting in a 50% insulin reduction being set for Cohort 2. Patients in Cohort 2 were randomized on day 1 in a 1:1:1 ratio to double-blind placebo, 10 mg dapagliflozin or 20 mg dapagliflozin once daily, in addition to their open-label OAD(s) and 50% of their usual daily insulin, that is an average of 52 to 54 units of insulin daily.

Patients were scheduled for visits at weeks 1, 2, 4, 6, 8, 10, and 12 of treatment, and performed SMBG 5 times daily during the 3 to 5 days prior to visits. No dose modifications of blinded study medication or OAD(s) were allowed during the treatment phase. Guidelines were in place throughout the trial for managing hypo- and hyperglycemia. In patients with or at risk of hypoglycemia, insulin could be down-titrated if SMBG levels were <54 mg/dL, mean daily glucose was <100 mg/dL, or clinical necessity as determined by the investigator. Additional down-titration could be implemented as clinically indicated to manage the risk of hypoglycemia. Discontinuation would occur if the patient experienced major hypoglycemia, defined as blood glucose values <54 mg/dL, at least one symptom (confusion/disorientation, abnormal behavior, or unconsciousness) and third party treatment with carbohydrate, glucose or glucagon.

Criteria for management of hyperglycemia were determined by fasting plasma glucose (FPG) measurements. For any FPG level >240 mg/dL at weeks 4 and 6, >220 mg/dL at week 8, or >200 mg/dL at week 10, the patient would be scheduled for a follow-up visit in 3 to 5 days. If FPG was still above the threshold at follow-up, a visit was scheduled in order to increase the insulin dose as clinically indicated. Patients who further lacked glycemic control despite up-titration, or whose modified insulin dose exceeded baseline, were discontinued from blinded treatment and entered into follow-up.

All patients completing the treatment phase or prematurely discontinued from treatment entered a 4 week safety observation period. Patients continued their open-label OAD(s) and insulin therapy with dose adjustments as needed, but did not receive further investigational therapy. Follow-up visits occurred at weeks 14 and 16.

Patient Population

Eligible patients were males and females with T2DM, 18 to 75 years old, with a BMI ≤45 kg/m², who had inadequate glycemic control (defined as $HbA_{1c} \geq 7.5\%$ and ≤10%). All patients were on insulin-sensitizer therapy for at least 6 weeks prior to enrollment and insulin-based therapy for at least 12 weeks prior to enrollment. The study protocol defined insulin-sensitizer therapy as metformin (stable dose ≥1000 mg) and/or pioglitazone (stable dose ≥30 mg) or rosiglitazone (stable dose 4 mg). Insulin-based therapy was defined as subcutaneous insulin for at least 12 weeks prior to enrollment, with 2 minimum insulin daily dose equivalent to 50 units (median 85 to 93 units across all study arms) of U100 insulin per day. The insulin regimen must have been stable for at least 6 weeks. In addition to 10 mg dapagliflozin or 20 mg dapagliflozin daily or placebo, 74.6% of patients received metformin (≥1000 mg daily) plus insulin; 16.9% of patients received metformin (≥1000 mg daily) plus pioglitazone (≥30 mg daily) or rosiglitazone (4 mg daily) plus insulin and 8.5% of patients received pioglitazone (≥30 mg daily) or rosiglitazone (4 mg daily) plus insulin.

Patients in Cohort 2 received an average of 52 to 54 units of insulin daily.

Laboratory criteria included fasting C-peptide ≥0.8 ng/mL; serum creatinine <1.5 mg/dL (male)/<1.4 mg/dL (female); and urine microalbumin/creatinine ratio<300 mg/g, or if exceeded on spot check, a 24-hour urine total protein <3 g/24 hours.

Major exclusion criteria were history of type 1 diabetes; AST and/or ALT >2.5×ULN; creatine kinase ≥3×ULN; symptoms of severely uncontrolled diabetes (including marked polyuria and polydipsia with >10% weight loss during the last 3 months before enrollment or other signs and symptoms); history of severe hypoglycemia or hypoglycemia unawareness; and unstable or serious cardiovascular, renal, hepatic, hematological, ontological, endocrine, psychiatric, or rheumatic diseases.

Trial Outcomes

Patients in Cohort 1 were evaluated for safety only. Patients in Cohort 2 were evaluated for safety and efficacy. The primary efficacy measure was change from baseline in $HbA_{1c}$, at week 12, last observation carried forward (LOCF). If no week 12 assessment was available, the last observation prior to week 12 was used. Secondary efficacy measures included changes from baseline at week 12 (LOCF) in FPG and insulin dose, the proportion of patients achieving a decrease in $HbA_{1c}$>0.5% from baseline at week 12 (LOCF), and the proportion of patients achieving $HbA_{1c}$<7% at week 12 (LOCF). Tertiary endpoints included changes from baseline in total body weight and in postprandial glucose (PPG) measured by an oral glucose tolerance test (OGTT).

Patients in Cohort 2 were evaluated for safety and efficacy. The primary efficacy measure was change from baseline in $HbA_{1c}$ at week 12, last observation carried forward (LOCF). The analysis was done excluding data after up-titration of insulin. If no week 12 assessment was available, the last observation prior to week 12 was used.

Safety outcomes were assessed by treatment-emergent adverse events, vital signs, ECGs and laboratory measurements, including 24-hour urine collections for volume and electrolytes.

Statistical Analysis and Sample Size

For Cohort 2, the sample size target of 22 patients per treatment group was chosen to allow for the calculation of 95% confidence intervals for the primary endpoint with a half-width of 0.42% for each treatment group. This assumed a 1% standard deviation for the primary endpoint in each of the dapagliflozin and placebo arms. With the same assumption, the half-width of a 95% confidence interval for the difference between any two treatment mean changes was estimated to be 0.59%. The primary efficacy data set consisted of all randomized patients who took at least one dose of double-blind study medication during the treatment phase. The analyses of the efficacy variables (except change from baseline in insulin dose) were done excluding data after up-titration of insulin. The analyses for changes from baseline in $HbA_{1c}$, FPG, insulin dose, and total body weight at week 12 (LOCF) were performed using an analysis of covariance (ANCOVA) model with treatment group as an effect and baseline value as a covariate. Point estimates and 95% confidence intervals were calculated for mean changes within each treatment group and for differences in mean changes between the dapagliflozin and placebo groups.

Main Outcome Measure

Change from baseline in glycated hemoglobin ($HbA_{1c}$) at week 12, last observation carried forward (LOCF).

Results

Patient Population

A total of 11 patients were screened for Cohort 1, and 163 screened for Cohort 2 at 26 sites in the United States and Canada. Four patients in Cohort 1 were assigned to single-blind dapagliflozin 20 mg. Seventy-one patients in Cohort 2 were randomized to the placebo, 10 mg and 20 mg dapagliflozin groups (23, 24, and 24 patients, respectively).

Summary of Results and Conclusions

At week 12 (LOCF), dapagliflozin 10 and 20 mg groups demonstrated −0.70% and −0.78% mean differences in change from baseline in $HbA_{1c}$, compared to placebo. In both dapagliflozin groups, 65.2% achieved a decrease from baseline in $HbA_{1c} \geq 0.5\%$ versus 15.8% in the placebo group. Mean changes from baseline in fasting plasma glucose (FPG) at week 12 (LOCF) were 17.8 mg/dL, 2.4 mg/dL, and −9.6 mg/dL (placebo, 10 and 20 mg dapagliflozin groups). Reductions in post-prandial glucose (PPG) with dapagliflozin, measured at 120 minutes by OGTT, also showed dose-dependency. Week 12 (LOCF) mean changes in total body weight were −1.9 kg, −4.5 kg, and −4.3 kg (placebo, 10 and 20 mg dapagliflozin groups).

Based on the results obtained, in insulin-resistant patients who had their baseline insulin reduced 50%, dapagliflozin decreased $HbA_{1c}$, PPG and weight more than placebo, and had a dose-dependent effect on FPG.

Detailed Discussion of Results

Table I summarizes efficacy outcomes for Cohort 2. In the 10 mg and 20 mg dapagliflozin treatment groups, there were decreases from baseline in $HbA_{1c}$, at week 12 (LOCF), resulting in differences in mean changes versus placebo of −0.70% and −0.78% (Table I). Table I shows mean changes in $HbA_{1c}$, at week 12 (LOCF). At week 12 (LOCF) 65.2% of the patients in both dapagliflozin groups achieved a decrease from baseline in $HbA_{1c}$ of at least 0.5% versus 15.8% in the placebo group (Table I). There was no appreciable change from baseline in total daily insulin dose. Five patients (1 each in the dapagliflozin 20 mg and placebo groups, and 3 in the 10 mg dapagliflozin group) showed a therapeutic response defined as $HbA_{1c}$<7% (Table I). Throughout the 12-week double-blind period, 4 patients in the placebo arm required up-titration of insulin, compared to 1 patient in the dapagliflozin 10 mg arm and 3 patients in the dapagliflozin 20 mg arm. In both dapagliflozin arms, 66.7% of patients were exposed to study medication for ≥84 days prior to insulin up-titration versus 39.1% of patients in the placebo arm.

Compared to placebo, the effect of dapagliflozin on FPG was dose-dependent (Table I). At week 12 (LOCF), the mean changes from baseline were 17.8 mg/dL, 2.4 mg/dL, and −9.6 mg/dL for the placebo, 10 mg and 20 mg dapagliflozin groups, respectively. PPG, measured at 120 minutes by OGTT, also showed dose-response characteristics (Table I). Dapagliflozin was more likely to lower weight than placebo. At week 12 (LOCF), mean change in total body weight was −1.9 kg with placebo, −4.5 kg with 10 mg dapagliflozin, and −4.3 kg with 20 mg dapagliflozin (Table I).

Vital Signs and Laboratory Outcomes

The placebo group experienced a slight increase in standing blood pressure at week 12, whereas both dapagliflozin groups demonstrated mean improvements in standing systolic and diastolic blood pressure (−7.2 systolic/−1.2 diastolic mm Hg [10 mg dapagliflozin], −6.1 systolic/−3.9 diastolic mm Hg [20 mg dapagliflozin]). In the 20 mg dapagliflozin group, supine blood pressure decreased (mean change of −5.5 systolic/−5.8 diastolic mm Hg)

Mean changes from baseline in urinary glucose excretion at week 12 were −1.5 g/24 h (placebo), 83.5 g/24 h (dapagliflozin 10 mg), and 85.2 g/24 h (dapagliflozin 20 mg). Mean 24-hour urine output increased from 1869.6 to 2124.6 mL with placebo, 1921.0 to 2285.8 mL with dapagliflozin 10 mg, and 1808.8 to 2253.1 mL with dapagliflozin 20 mg. Compared to baseline, glomerular filtration rates at the end of treatment were normal, with minor changes of −0.58, −0.84, and 1.45 mL/min/1.73 m$^2$ in the respective placebo and dapagliflozin 10 and 20 mg groups. Generally, there were no remarkable changes from baseline in key laboratory parameters. Median change from baseline in serum uric acid was −0.30 mg/dL in both dapagliflozin groups. Median increases from baseline in serum hematocrit at week 12 were 2.5% and 3.05% in the dapagliflozin 10 and 20 mg groups, respectively.

Safety and Adverse Events

Adverse events were balanced across all groups, reported in 65.2%, 75.0% and 66.7% of patients in the placebo, 10 mg and 20 mg dapagliflozin arms, respectively. Three patients in the placebo group, seven patients in the dapagliflozin 10 mg group, and six patients in the 20 mg dapagliflozin group reported episodes of hypoglycemia. Of these, one patient in the placebo group reported major hypoglycemia. There were no deaths in this study, and two patients experienced a serious adverse event (one in the placebo group and one in the dapagliflozin 20 mg group). One patient in each of the three treatment arms experienced adverse events that led to discontinuation.

Six patients experienced genital tract infections during the double-blind period: five in the 20 mg dapagliflozin group, one in the placebo group, and none in the 10 mg dapagliflozin group. One patient in the dapagliflozin 20 mg group reported a urinary tract infection.

Events of pollakiuria were reported across all treatment groups: four patients (placebo), two patients (10 mg dapagliflozin), and three patients (20 mg dapagliflozin). One patient in each of the dapagliflozin arms reported polyuria. One case of microalbuminuria in the dapagliflozin 20 mg arm resulted in discontinuation from the study.

One event of pre-renal azotemia occurred during treatment with 10 mg dapagliflozin. The patient was being chronically treated with multi antihypertensives, including enalapril, carvedilol and furosemide. Eleven days after starting study medication, the patient was discontinued from the study due to dehydration and pre-renal azotemia. Furosemide and enalapril therapy were held, and the pre-renal azotemia resolved with oral rehydration.

Comment

Disease progression in T2DM is frequently accompanied by a cycle of deteriorating glycemic control due to declining beta cell function and the progressive failure of insulin secretion, increasing weight that exacerbates existing insulin resistance, and the need for additional therapies. Therapies that depend on insulin supplementation or secretion entail the risk of hypoglycemia, weight gain, decreased insulin sensitivity, and eventual loss of effectiveness. Identifying effective treatment modalities is therefore difficult. This frustrating clinical setting is exemplified most dramatically by late stage T2DM patients who require high doses of insulin, often with oral agents such as metformin and/or TZDs, in order to maintain glycemic control, albeit at the expense of perpetuating the cycle of inadequate glycemic control, increasing insulin resistance, and escalating insulin dose requirements. Ultimately, over 25% of patients end up being treated with insulin-based regimens, often in combination with OADs. (Koro, C. E. et al., "Glycetnic control from 1988 to 2000 among U.S. adults diagnosed with type 2 diabetes: a preliminary report", *Diabetes Care*, 27 (1):17-20 (2004)). A novel strategy for controlling glycemia independently of insulin involves limiting glucose reabsorption in the proximal tubules of the kidney where glucose is reabsorbed via SGLT2 receptors. Dapagliflozin selectively inhibits SGLT2, thereby limiting glucose reabsorption and inducing dose-dependent glucosuria.

Patients recruited for this study had inadequate glycemic control despite aggressive regimens of insulin plus OADs. After reducing the insulin dose by 50% in this highly insulin-resistant population, patients in the placebo arm experienced weight loss but very little change in $HbA_{1c}$, highlighting the limited additional benefit afforded by increasing insulin dose in this population. Treatment with dapagliflozin, with its insulin-independent mechanism of action, was associated with additional weight loss of −2.5 kg, and with improvements in glycemic control compared to placebo. Although total hypoglycemic events were more frequently reported with dapagliflozin treatment than with placebo, major/minor episodes were balanced across all groups.

The reductions in $HbA_{1c}$ with dapagliflozin, and improvements over placebo in FPG and PPG, were dose-dependent. Dose-dependency also appeared to be a feature of the potential safety signal of genital tract infections, more frequently seen in the 20 mg dose arm. The apparent dose-response relationship seen for these parameters, however, was not evident for the main pharmacodynamic measure, 24-hour urinary glucose, which increased by ~85 grams per day at week 12 in both the 10 mg and the 20 mg dapagliflozin groups. A plausible explanation is that 20 mg dapagliflozin may have caused greater glucosuria than 10 mg earlier in the study, as has been seen in other settings (Komoroski, B. et al., supra; List, J. F. et al., supra; Komoroski, B. et al., "Dapagliflozin, a novel SGLT2 inhibitor, induces dose-dependent glucosuria in healthy subjects", *Clin. Pharmacol. Ther.*, 85 (5):520-526 (2009)), but that the resulting greater declines in glycemia in the 20 mg dose group led to a lower filtered load of glucose at the kidney, such that by week 12 the amount of glucose in the urine had equalized between the dapagliflozin dose groups.

The subject study establishes the proof of concept that re-establishing glucosuria in a controlled pharmacologic manner can break the upward spiral of insulin dosing in highly insulin-resistant patients, allowing for improved glycemic control and weight loss in the setting of a large insulin dose reduction (50%).

TABLE I

Baseline, On-Treatment, and Change from Baseline in Efficacy Parameters for Randomized Patients in Cohort 2 (n = 71)

| Parameter | Placebo + Insulin[h] + OAD[i] (n = 23)[a] | | Dapagliflozin 10 mg + Insulin[h] + OAD[i] (n = 24)[a] | | Dapagliflozin 20 mg + Insulin[h] + OAD[i] (n = 24)[1] | |
|---|---|---|---|---|---|---|
| | No.[b] | Value | No.[b] | Value | No.[b] | Value |
| Baseline | | | | | | |
| $HbA_{1c}$, mean (SD), % | 19 | 8.3 (0.8) | 23 | 8.4 (0.7) | 23 | 8.5 (0.9) |
| Fasting plasma glucose, mean (SD), mg/dL | 22 | 166.8 (52.6) | 23 | 155.7 (39.8) | 23 | 157.9 (53.0) |
| Total daily insulin dose after 50% down-titration on day 1, mean (SD), U | 22 | 54.1 (27.3) | 24 | 52.4 (24.4) | 24 | 54.5 (36.3) |
| Postprandial glucose, mean (SD), mg/dL[c] | 15 | 312.6 (82.2) | 19 | 320.2 (51.4) | 18 | 314.5 (71.8) |
| Weight, mean (SD), kg | 22 | 101.3 (16.7) | 23 | 102.8 (9.9) | 23 | 102.1 (15.0) |
| End of Double-blind (Week 12 LOCF) | | | | | | |
| $HbA_{1c}$, mean (SD), %[d] | 19 | 8.5 (0.8) | 23 | 7.8 (0.7) | 23 | 7.8 (0.6) |
| Patients with ↓ $HbA_{1c}$ ≥ 0.5%, No. (%), response[d] | 19 | 3 (15.8) | 23 | 15 (65.2) | 23 | 15 (65.2) |
| Patients with $HbA_{1c}$ < 7.0% No. (%), response[d] | 19 | 1 (5.3) | 23 | 3 (13.0) | 23 | 1 (4.3 |
| Fasting plasma glucose, mean (SD), mg/dL[d] | 22 | 180.8 (56.9) | 23 | 160.5 (38.7) | 23 | 149.4 (32.0) |
| Total daily insulin dose, mean (SD), U[e] | 22 | 55.7 (26.5) | 24 | 51.3 (20.1) | 24 | 53.5 (32.1) |
| Postprandial glucose, mean (SD), mg/dL[c,d] | 15 | 331.3 (46.8) | 19 | 286.0 (55.1) | 18 | 272.6 (51.2) |
| Weight, mean (SD), kg[d] | 22 | 99.4 (16.7) | 23 | 98.2 (9.4) | 23 | 97.8 (14.1) |
| Change from Baseline and Differences versus Placebo + Insulin + OAD | | | | | | |
| $HbA_{1c}$, mean (95% CI), %[d,f] | 19 | 0.09 (−0.19 to 0.37) | 23 | −0.61 (−0.87 to −0.36) | 23 | −0.69 (−0.94 to −0.43) |
| Difference vs placebo + insulin + OAD, mean (95% CI), % | | | | −0.70 (−1.08 to −0.32) | | −0.78 (−1.16 to −0.40) |
| Patients with ↓ $HbA_{1c}$ ≥ 0.5%, difference in proportions vs placebo + insulin + OAD (95% CI), % | | | | 49.4 (20.1 to 72.4) | | 49.4 (20.1 to 72.4) |
| Fasting plasma glucose, mean (95% CI), mg/dL[d,f] | 22 | 17.8 (1.4 to 34.2) | 23 | 2.4 (−13.6 to 18.3) | 23 | −9.6 (−25.6 to 6.3) |
| Difference vs placebo + insulin + OAD, mean (95% CI), mg/dL | | | | −15.4 (−38.4 to 7.5) | | −27.4 (−50.3 to −4.6) |
| Total daily insulin dose, mean (95% CI, U[e,f] | 22 | 1.7 (−3.8 to 7.2) | 24 | −1.4 (−6.6 to 3.9) | 24 | −0.8 (−6.1 to 4.5) |
| Difference vs placebo + insulin + OAD, mean (95% CI), U | | | | −3.1 (−10.7 to 4.6) | | −2.5 (−10.2 to 5.1) |
| Postprandial glucose, mean (95% CI), mg/dL[c,d] | 15 | 18.7 (−13.5 to 50.9) | 19 | −34.3 (−67.5 to −1.1) | 18 | −41.9 (−74.8 to −8.9) |
| Weight, mean (95% CI), kg[d,f] | 22 | −1.9 (−2.9 to −0.9) | 23 | −4.5 (−5.5 to −3.5) | 23 | −4.3 (−5.3 to −3.3) |
| Difference vs placebo + insulin + OAD, mean (95% CI), kg | | | | −2.6 (−4.0 to −1.2) | | −2.4 (−3.8 to −1.0) |

Abbreviations:
CI, confidence interval;
$HbA_{1c}$, glycated hemoglobin;
OGTT, oral glucose tolerance test;
SD, standard deviation;
U, units of U100 insulin
[a] Number of randomized patients who took at least one dose of the double-blind study medication.
[b] Number of patients with non-missing baseline and week 12 (last observation carried forward) values.
[c] Postprandial glucose measured at 120 minutes by oral glucose tolerance test.
[d] Excludes data after insulin up-titration.
[e] Includes data after insulin up-titration.
[f] Adjusted change from baseline based on an ANCOVA model with treatment group as an effect and baseline value as a covariate.
[g] 95% exact CI for difference in proportions of patients achieving HbA1, therapeutic response.
[h] Average daily insulin of 52 to 54 units.
[i] OAD = oral antidiabetic medication - 74.6% of patients received ≥1000 mg metformin daily; 16.9% received ≥1000 mg metformin daily plus pioglitazone (≥30 mg daily) or rosiglitazone (4 mg daily); and 8.5% of patients received pioglitazone (≥30 mg daily) or rosiglitazone (4 mg daily).

What is claimed is:

1. A method for treating extreme insulin resistance in a mammalian patient, wherein the patient has previously been treated with ≥50 units of insulin per day and at least one or more of metformin, pioglitazone, or rosiglitazone, and wherein the previous treatment provided inadequate glycemic control ($HbA_{1c}$<7%) the method comprising:
    administering to said patient in need of treatment a therapeutically effective amount of an SGLT2 inhibitor of formula:

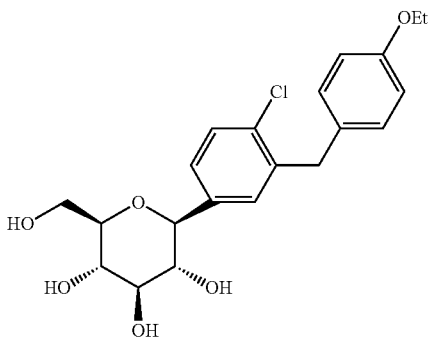 [SMILES: CCOc1ccc(Cc2cc([C@@H]3O[C@H](CO)[C@@H](O)[C@H](O)[C@H]3O)ccc2Cl)cc1]

or a prodrug ester thereof or a propylene glycol solvate thereof.

2. The method as defined in claim 1 wherein the patient is treated with the SGLT2 inhibitor in combination with one or more of insulin, metformin, glyburide, glipizide, pioglitazone, rosiglitazone, saxagliptin, vildagliptin, sitagliptin or exenatide.

3. The method as defined in claim 1 wherein the SGLT2 inhibitor is administered in an amount within the range from about 0.5 to about 350 mg/day.

4. The method as defined in claim 2 wherein the patient is treated with an SGLT2 inhibitor in combination with
    a) insulin; or
    b) insulin and metformin; or
    c) insulin and a thiazolidinedione; or
    d) insulin and metformin and a thiazolidinedione.

5. The method according to claim 1, wherein the SGLT2 inhibitor is:

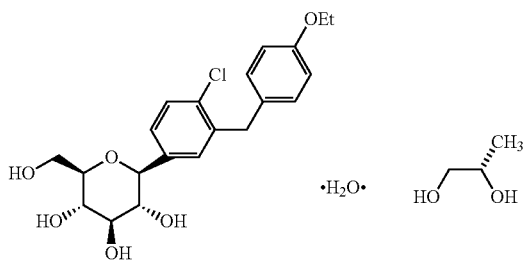

6. The method as defined in claim 4 wherein the SGLT2 inhibitor is
    (a) dapagliflozin or dapagliflozin-PGS at a dose from about 0.5 to about 200 mg/day is administered in combination with insulin at a dose as prescribed by a physician or as described in the PDR; or
    (b) dapagliflozin or dapagliflozin-PGS at a dose from about 0.5 to about 200 mg/day is administered in combination with insulin at a dose as prescribed by a physician or as described in the PDR, and metformin at a dose from about 500 to about 2000 mg/day; or
    (c) dapagliflozin or dapagliflozin-PGS at a dose from about 0.5 to about 200 mg/day is administered in a combination with insulin at a dose as prescribed by a physician or as described in the PDR, pioglitazone at a dose from about 0.5 to about 75 mg/day, or rosiglitazone at a dose from about 0.5 to about 25 mg/day; or
    (d) dapagliflozin or dapagliflozin-PGS at a dose from about 0.5 to about 200 mg/day is administered in combination with insulin at a dose as prescribed by a physician or as described in the PDR, metformin at a dose from about 500 to about 2000 mg/day, and pioglitazone at a dose from about 0.5 to about 75 mg/day or rosiglitazone at a dose from about 0.5 to about 25 mg/day.

7. The method according to claim 1, wherein the SGLT2 inhibitor is administered at a dose from about 0.5 to about 350 mg, in combination with:
    a) metformin; or
    b) pioglitazone or rosiglitazone; or
    c) insulin; or
    d) metformin and insulin; or
    e) pioglitazone or rosiglitazone and metformin; or
    f) pioglitazone or rosiglitazone and insulin; or
    g) metformin, pioglitazone or rosiglitazone and insulin.

8. A method for providing glycemic control ($HbA_{1c}$<7.0%) to a patient, wherein glycemic control is not achievable using one or more of insulin, metformin, pioglitazone, or rosiglitazone, the method comprising administering to said patient a therapeutically effective amount of an SGLT2 inhibitor of formula:

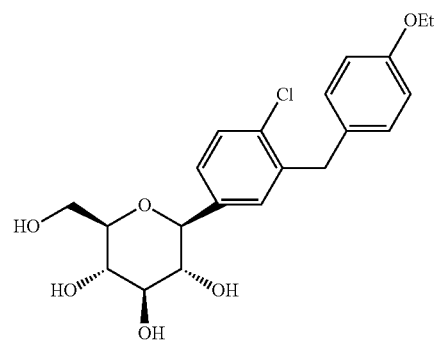 [SMILES: CCOc1ccc(Cc2cc([C@@H]3O[C@H](CO)[C@@H](O)[C@H](O)[C@H]3O)ccc2Cl)cc1]

or a prodrug ester thereof or a propylene glycol solvate thereof.

9. A method according to claim 8, wherein the SGLT2 inhibitor is:

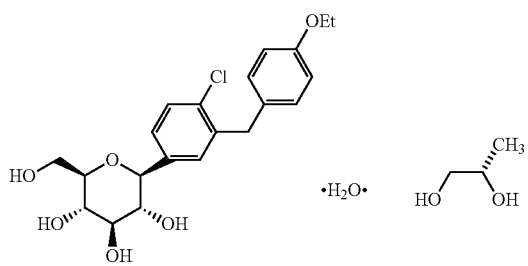

10. The method as defined in claim 8 wherein the SGLT2 inhibitor is
  (a) dapagliflozin or dapagliflozin-PGS at a dose from about 0.5 to about 200 mg/day is administered in combination with insulin at a dose as prescribed by a physician or as described in the *Physicians' Desk Reference* (PDR); or
  (b) dapagliflozin or dapagliflozin-PGS at a dose from about 0.5 to about 200 mg/day is administered in combination with insulin at a dose as prescribed by a physician or as described in the PDR, and metformin at a dose from about 500 to about 2000 mg/day; or
  (c) dapagliflozin or dapagliflozin-PGS at a dose from about 0.5 to about 200 mg/day is administered in a combination with insulin at a dose as prescribed by a physician or as described in the PDR, pioglitazone at a dose from about 0.5 to about 75 mg/day, or rosiglitazone at a dose from about 0.5 to about 25 mg/day; or
  (d) dapagliflozin or dapagliflozin-PGS at a dose from about 0.5 to about 200 mg/day is administered in combination with insulin at a dose as prescribed by a physician or as described in the PDR, metformin at a dose from about 500 to about 2000 mg/day, and pioglitazone at a dose from about 0.5 to about 75 mg/day or rosiglitazone at a dose from about 0.5 to about 25 mg/day.

11. A method according to claim 8, wherein the patient further has extreme insulin resistance.

12. A method according to claim 11, wherein ≥50 units of insulin per day and at least one or more of metformin, pioglitazone, or rosiglitazone was ineffective to provide adequate glycemic control ($HbA_{1c}$<7%).

13. A method according to claim 8, wherein the SGLT2 inhibitor is administered in an amount within the range from about 0.5 to about 350 mg/day.

* * * * *